United States Patent [19]

DiNinno et al.

[11] Patent Number: 5,292,879
[45] Date of Patent: * Mar. 8, 1994

[54] INTERMEDIATES FOR PREPARING CATIONIC-2-HETEROARYL-PHENYL-CARBAPENEM ANTIBACTERIAL AGENTS

[75] Inventors: Frank DiNinno, Old Bride; Ravindra N. Guthikonda, Edison; Susan M. Schmitt, Scotch Plains, all of N.J.

[73] Assignee: Merck & Co., Inc., Rahway, N.J.

[*] Notice: The portion of the term of this patent subsequent to Sep. 1, 2009 has been disclaimed.

[21] Appl. No.: 937,632

[22] Filed: Aug. 28, 1992

[51] Int. Cl.$^5$ ............................................. C07D 487/04
[52] U.S. Cl. ........................................................ 540/302
[58] Field of Search ............................................ 540/302

[56] References Cited

U.S. PATENT DOCUMENTS

| | | |
|---|---|---|
| 4,260,627 | 4/1981 | Christensen et al. ............... 540/302 |
| 4,465,632 | 8/1984 | Christensen et al. ............... 540/302 |
| 4,543,257 | 9/1985 | Cama et al. ........................ 540/302 |
| 4,729,993 | 3/1988 | Christensen et al. ............... 540/302 |
| 4,775,669 | 10/1988 | Cama et al. ...................... 540/302 |
| 4,962,101 | 10/1990 | DiNinno et al. .................... 540/302 |
| 4,978,659 | 12/1990 | DiNinno et al. .................... 540/302 |
| 5,004,739 | 4/1991 | DiNinno et al. .................... 540/302 |
| 5,004,740 | 4/1991 | DiNinno et al. .................... 540/302 |
| 5,006,519 | 4/1991 | DiNinno et al. .................... 540/302 |
| 5,011,832 | 4/1991 | DiNinno et al. .................... 540/302 |
| 5,025,006 | 6/1991 | DiNinno et al. .................... 540/302 |
| 5,025,007 | 6/1991 | Greenlee et al. ................... 540/302 |
| 5,025,008 | 6/1991 | DiNinno et al. .................... 540/302 |
| 5,032,587 | 7/1991 | DiNinno et al. .................... 540/302 |
| 5,034,384 | 7/1991 | Greenlee et al. ................... 540/302 |
| 5,034,385 | 7/1991 | DiNinno et al. .................... 540/302 |
| 5,037,820 | 8/1991 | DiNinno et al. .................... 540/302 |
| 5,128,335 | 7/1992 | Guthikonda et al. ............... 540/302 |
| 5,132,421 | 7/1992 | DiNinno et al. .................... 540/302 |
| 5,132,422 | 7/1992 | DiNinno et al. .................... 540/302 |
| 5,143,914 | 9/1992 | DiNinno ............................. 514/210 |
| 5,144,028 | 9/1992 | Greenlee et al. ................... 540/302 |

OTHER PUBLICATIONS

L. D. Cama et al., Total Synthesis of Theinamycin Analogs–III, Tetrahedron 39, 2531 (1983).

R. N. Guthikonda, et al., Structure Activity Relationship in the 2-Arylcarbapenem Series, *J. Med. Chem.*, 30, 871 (1987).

Primary Examiner—Robert Gerstl
Attorney, Agent, or Firm—Mark R. Daniel; Joseph F. DiPrima

[57] ABSTRACT

Carbapenem compounds of the formula

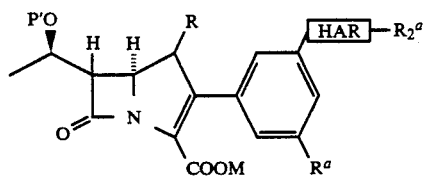

are useful intermediates for preparing antibacterial agents.

6 Claims, No Drawings

INTERMEDIATES FOR PREPARING CATIONIC-2-HETEROARYL-PHENYL-CARBAPENEM ANTIBACTERIAL AGENTS

BACKGROUND OF THE INVENTION

The present invention relates to antibacterial agents of the carbapenem class, in which the 2-position sidechain is characterized by a heteroarylphenyl moiety, substituted by various cationic and neutral substituents, as described in more detail below.

Thienamycin was an early carbapenem antibacterial agent having a broad spectrum; it has the following formula:

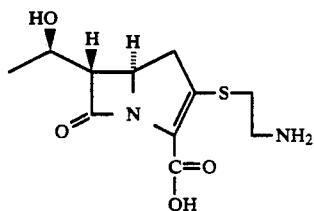

Later, N-formimidoyl thienamycin was discovered; it has the formula:

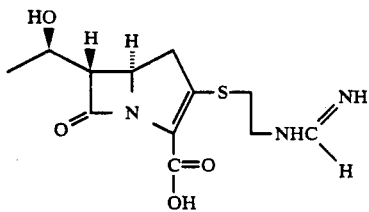

The cationic 2-heteroarylphenyl-carbapenems of the present invention are not characterized by a broad antibacterial spectrum such as that of thienamycin or N-formimidoyl thienamycin. Rather, their spectrum of activity is largely limited to gram positive microorganisms, especially methicillin resistant *Staphylococcus aureus* (MRSA), methicillin resistant *Staphylococcus epidermidis* (MRSE), and methicillin resistant coagulase negative Staphylococci (MRCNS). The antibacterial compounds of the present invention thus comprise an important contribution to therapy of these difficult to control pathogens. Moreover, there is an increasing need for agents effective against such pathogens (MRSA/MRCNS) which are at the same time safe, i.e., free from undesirable toxic side effects. No β-lactam antibacterial has yet been found which meets these requirements. And, the current agent of choice, vancomycin, a glycopeptide antibacterial, is experiencing an ever increasing amount of resistance in the MRSA/MRCNS pathogens.

More recently, carbapenem antibacterial agents have been described which have a 2-substituent which is an aryl moiety optionally substituted by, e.g., aminomethyl and substituted aminomethyl. These agents are described in U.S. Pat. Nos. 4,543,257 and 4,260,627 and have the formula:

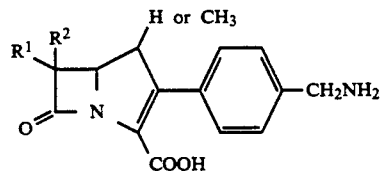

However, there is no description or suggestion of a cationic heteroarylphenyl 2-substituent such as characterizes the compounds of the present invention, nor is there any suggestion of the surprisingly better anti-MRSA/MRCNS activity of the compounds of the present invention.

U.S. Pat. No. 4,978,659 describes a particular class of compounds of the formula:

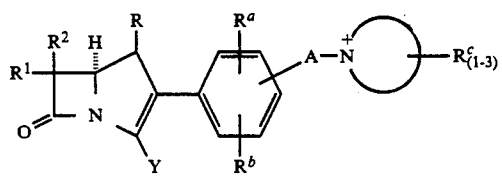

but this limited teaching in no way suggests the totally different compounds of the present invention, nor their surprisingly better anti-MRSA/MRCNS activity.

SUMMARY OF THE INVENTION

The present invention provides novel carbapenem compounds of the formula:

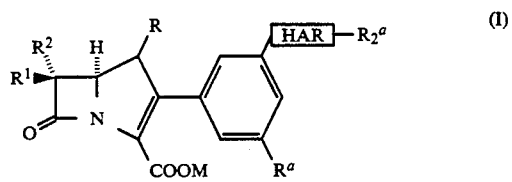

wherein:

R is H or CH$_3$;

R$^1$ and R$^2$ are independently H, CH$_3$—, CH$_3$CH$_2$—, (CH$_3$)$_2$CH—, HOCH$_2$—, CH$_3$CH(OH)—, (CH$_3$)$_2$C(OH)—, FCH$_2$CH(OH)—, F$_2$CHCH(OH)—, F$_3$CCH(OH)—, CH$_3$CH(F)—, CH$_3$CF$_2$—, or (CH$_3$)$_2$C(F)—;

HAR is a 5- or 9-membered mono- or bicyclic heteroaryl ring system wherein 1 atom is O or S, or an 8-membered bicyclic heteroaryl ring system wherein 2 atoms are O and/or S;

R$^a$ is each independently selected from the group consisting of hydrogen and the radicals set out below, provided that one and only one R$^a$ is selected from Type I substituents:

I.

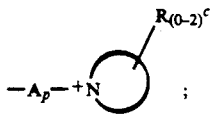

where is $(CH_2)_m$—Q—$(CH_2)_n$, where m is 0 to 6 and n is 1 to 6 and Q is a covalent bond, O, S, SO, $SO_2$, NH, $-SO_2NH-$, $-NHSO_2-$, $-CONH-$, $-NHCO-$, $-SO_2N(C_1-C_4 \text{ alkyl})-$, $-N(C_1-C_4 \text{ alkyl})SO_2-$, $-CON(C_1-C_4 \text{ alkyl})-$, $-N(C_1-C_4 \text{ alkyl})CO-$, $-CH=CH-$, $-CO-$, $-OC(O)-$, $-C(O)O-$ or $N(C_1-C_4 \text{ alkyl})$ and $(CH_2)_m$ is attached to the phenyl aromatic moiety;

is a 5- or 6-membered monocyclic heterocycle or an 8-, 9- or 10-membered bicyclic heterocycle, the heterocycle containing a first nitrogen in an aromatic 5- or 6-membered first ring, with attachment of the heterocycle to A by way of said first nitrogen and said first nitrogen is quaternary by virtue of the attachment and ring bonds, with the first ring containing 0 or 1 of either O or S, with the first ring containing 0 to 3 additional nitrogen atoms, with the first ring optionally fused to a 3- or 4-membered moiety to form the optional second ring, with the moiety containing at least one carbon atom, with the moiety containing 0 or 1 of either O or S, with the moiety containing 0 to 2 nitrogen atoms, and with the moiety being saturated or unsaturated and the second ring aromatic or non-aromatic;

is $R^a$ as defined under II below, hydrogen, or $-NR^yR^z$ (where $R^y$ and $R^z$ are defined in II below), but independently selected from $R^a$ and from each other if more than one $R^c$ is present, and is attached to a carbon ring atom or a nitrogen heteroatom the valency of which is not satisfied by the ring bonds;

p is 0 or 1;

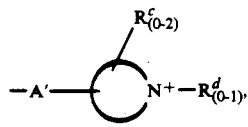

where

is a 5- or 6-membered monocyclic heterocycle or an 8-, 9- or 10-membered bicyclic heterocycle, the heterocycle containing a first nitrogen in an aromatic 5- or 6-membered first ring, with said first nitrogen quaternary by virtue of a substituent $R^d$ in addition to the ring bonds thereto, with said first nitrogen neutral in the absence of a substituent $R^d$, with attachment of the heterocycle to A' by way of a carbon atom of a ring, with the first ring containing 0 or 1 of either O or S, with the first ring containing 0 to 2 additional nitrogen atoms, with the first ring optionally fused to a 3- or 4-membered moiety to form the optional second ring, with the moiety containing at least one carbon atom, with the moiety containing 0 or 1 of either O or S, with the moiety containing 0 to 2 nitrogen atoms, and with the moiety being saturated or unsaturated and the second ring aromatic or non-aromatic;

$R^c$ is defined above;

$R^d$ is hydrogen, $NH_2$, $O^-$ or $C_1-C_4$ alkyl (where the alkyl group is optionally mono-substituted with $R^q$ as defined under IIc below);

A' is $(CH_2)_m$—Q—$(CH_2)_n$, where m is 0 to 6 and n is 0 to 6 and Q is defined above;

c) $-A_p-N^+R^y(R^w)_{0-1}(R^z)$, where $R^y$ and $R^z$ are defined under II below, $R^y$ and $R^z$ may further be together a $C_2-C_4$ alkylidene radical to form a ring (optionally mono-substituted with $R^q$ as defined below) interrupted by $N(O)R^e$ or $N^+(R^e)_2$ (where $R^e$ is hydrogen, $C_1-C_4$ alkyl, or $C_1-C_4$ alkyl mono-substituted with $R^q$ as defined below), $R^w$ is hydrogen, $C_{1-4}$ alkyl, $O^-$, $NH_2$, or absent in which case the $N^+$ is neutral, $R^w$, $R^y$ and $R^z$ may further together form a $C_5-C_{10}$ tertiary alkylidene radical which with $N^+$ forms a bicyclic ring, where the tertiary alkylidene radical is optionally mono-substituted with $R^q$ as defined below and where the tertiary carbon of the tertiary alkylidene radical is optionally replaced with nitrogen, $N^+R^e$ (where $R^e$ is defined above), or $N^+-O^-$, p is 0 or 1, and A is as defined above;

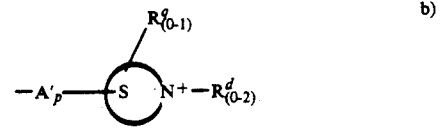

where

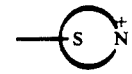

is a 5- or 6-membered monocyclic heterocycle or an 8-, 9- or 10-membered bicyclic heterocycle, the heterocycle containing a first nitrogen in a first ring, with the first ring saturated or unsaturated and non-aromatic, with the first nitrogen quaternary by virtue of one or two substituents $R^d$ in addition to the ring bonds thereto, with the first nitrogen alternatively neutral by virtue of zero or one substituents $R^d$ in addition to the ring bonds thereto with attachment of the heterocycle to A' by way of a carbon atom or non-quaternary nitrogen atom of a ring, with the first ring containing in addition to carbon and the first nitrogen 0 to 1 of a member selected from the group consisting of the non-quaternary nitrogen of attachment, O, S, S(O), $S(O)_2$ and $NR^e$ where $R^e$ is defined above, with the first ring optionally fused to a 2-, 3- or 4-membered moiety to form the optional second ring, with the moiety optionally containing in addition to carbon the non-quaternary nitrogen of attachment, and with the moiety saturated or unsaturated and the second ring non-aromatic;

$R^d$ is defined above and where more than one $R^d$ is present on a nitrogen, at least one $R^d$ is hydrogen or $C_1$-$C_4$ alkyl;

A' is defined above; and p is defined above;

$R^q$ is defined below;

II.

a) a trifluoromethyl group: —$CF_3$;

b) a halogen atom: —Br, —Cl, —F, or —I;

c) $C_1$-$C_4$ alkoxy radical: —$OC_{1-4}$ alkyl, wherein the alkyl is optionally mono-substituted by $R^q$, where $R^q$ is a member selected from the group consisting of —OH, —$OCH_3$, —CN, —$C(O)NH_2$, —$OC(O)NH_2$, CHO, —$OC(O)N(CH_3)_2$, —$SO_2NH_2$, —$SO_2N(CH_3)_2$, —$SOCH_3$, —$SO_2CH_3$, —F, —$CF_3$, —$COOM^a$ (where $M^a$ is hydrogen, alkali metal, methyl or phenyl), tetrazolyl (where the point of attachment is the carbon atom of the tetrazole ring and one of the nitrogen atoms is mono-substituted by $M^a$ as defined above) and —$SO_3M^b$ (where $M^b$ is hydrogen or an alkali metal);

d) a hydroxy group: —OH;

e) a carbonyloxy radical: —O(C=O)$R^s$, where $R^s$ is $C_1$-$C_4$ alkyl or phenyl, each of which is optionally mono-substituted by $R^q$ as defined above or tri-substituted with —F;

f) a carbamoyloxy radical: —O(C=O)N($R^y$)$R^z$, where $R^y$ and $R^z$ are independently H, $C_{1-4}$ alkyl (optionally mono-substituted by $R^q$ as defined above), together a 3- to 5-membered alkylidene radical to form a ring (optionally substituted with $R^q$ as defined above) or together a 2- to 4-membered alkylidene radical, interrupted by —O—, —S—, —S(O)—, —S(O)$_2$— or —$NR^e$—, to form a ring (where $R^e$ is hydrogen, $C_1$-$C_4$ alkyl, and $C_1$-$C_4$ alkyl mono-substituted with $R^q$ and the ring is optionally mono-substituted with $R^q$ as defined above);

g) a sulfur radical: —S(O)$_n$—$R^s$ where n=0-2, and $R^s$ is defined above;

h) a sulfamoyl group: —$SO_2$N($R^y$)$R^z$ where $R^y$ and $R^z$ are as defined above;

i) azido: $N_3$ j) a formamido group: —N($R^t$)—C(O)H, where $R^t$ is H or $C_1$-$C_4$ alkyl, and the alkyl thereof is optionally mono-substituted by $R^q$ as defined above;

k) a ($C_1$-$C_4$ alkyl)carbonylamino radical: —N($R^t$)—C(O)$C_1$-$C_4$ alkyl, where $R^t$ is as defined above, and the alkyl group is also optionally mono-substituted by $R^q$ as defined above;

a ($C_1$-$C_4$ alkoxy) carbonylamino radical: —N($R^t$)—C(O)O$C_1$-$C_4$ alkyl, where $R^t$ is as defined above, and the alkyl group is also optionally mono-substituted by $R^q$ as defined above;

m) a ureido group: —N($R^t$)—C(O)N($R^y$)$R^z$ where $R^t$, $R^y$ and $R^z$ are as defined above;

n) a sulfonamido group: —N($R^t$)$SO_2R^s$, where $R^s$ and $R^t$ are as defined above;

o) a cyano group: —CN;

p) a formyl or acetalized formyl radical: —C(O)H or —C(OCH$_3$)$_2$H;

q) ($C_1$-$C_4$ alkyl)carbonyl radical wherein the carbonyl is acetalized: —C(OCH$_3$)$_2C_1$-$C_4$ alkyl, where the alkyl is optionally mono-substituted by $R^q$ as defined above;

r) carbonyl radical: —C(O)$R^s$, where $R^s$ is as defined above;

s) a hydroximinomethyl radical in which the oxygen or carbon atom is optionally substituted by a $C_1$-$C_4$ alkyl group: —C($R^y$)=NO$R^z$ where $R^y$ and $R^z$ are as defined above, except they may not be joined together to form a ring;

t) a ($C_1$-$C_4$ alkoxy)carbonyl radical: —C(O)O$C_{1-4}$ alkyl, where the alkyl is optionally mono-substituted by $R^q$ as defined above;

u) a carbamoyl radical: —C(O)N($R^y$)$R^z$ where $R^y$ and $R^z$ are as defined above;

v) an N-hydroxycarbamoyl or N($C_1$-$C_4$ alkoxy)carbamoyl radical in which the nitrogen atom may be additionally substituted by a $C_1$-$C_4$ alkyl group: —(C=O)—N(O$R^y$)$R^z$ where $R^y$ and $R^z$ are as defined above, except they may not be joined together to form a ring;

w) a thiocarbamoyl group: —C(S)N($R^y$)($R^z$) where $R^y$ and $R^z$ are as defined above;

x) carboxyl: —$COOM^b$, where $M^b$ is as defined above;

y) thiocyanate: —SCN;

z) trifluoromethylthio: —$SCF_3$;

aa) tetrazolyl, where the point of attachment is the carbon atom of the tetrazole ring and one of the nitrogen atoms is mono-substituted by hydrogen, an alkali metal or a $C_1$-$C_4$ alkyl optionally substituted by $R^q$ as defined above;

ab) an anionic function selected from the group consisting of: phosphono [P=O(O$M^b$)$_2$]; alkylphosphono {P=O(O$M^b$)-[O($C_1$-$C_4$ alkyl)]}; alkylphosphinyl [P=O(O$M^b$)-($C_1$-$C_4$ alkyl)]; phosphoramido [P=O-(O$M^b$)N($R^y$)$R^z$ and P=O(O$M^b$)NH$R^x$]; sulfino (SO$_2M^b$); sulfo (SO$_3M^b$); acylsulfonamides selected from the structures CON$M^b$SO$_2R^x$, CON$M^b$SO$_2$N-($R^y$)$R^z$, SO$_2$N$M^b$CON($R^y$)$R^z$; and SO$_2$N$M^b$CN, where $R^x$ is phenyl or heteroaryl, where heteroaryl is a monocyclic aromatic hydrocarbon group having 5 or 6 ring atoms, in which a carbon atom is the point of attachment, in which one of the carbon atoms has been replaced by a nitrogen atom, in which one additional carbon atom is optionally replaced by a heteroatom selected from O or S in the case of a 5-membered ring, and in which from 1 to 2 additional carbon atoms are optionally replaced by a nitrogen heteroatom, and where the phenyl and heteroaryl are optionally mono-substituted by $R^q$, as defined above; $M^b$ is as defined above; and $R^y$ and $R^z$ are as defined above;

ac) $C_5$-$C_7$ cycloalkyl group in which one of the carbon atoms in the ring is replaced by a heteroatom selected from O, S, NH or N($C_1$-$C_4$ alkyl) and in which one additional carbon atom may be replaced by NH or N($C_1$-$C_4$ alkyl), and in which at least one carbon atom adjacent to each nitrogen heteroatom has both of its attached hydrogen atoms replaced by one oxygen thus forming a carbonyl moiety and there are one or two carbonyl moieties present in the ring;

ad) $C_2$-$C_4$ alkenyl radical, optionally mono-substituted by one of the substituents a) to ac) above and phenyl which is optionally substituted by $R^q$ as defined above;

ae) $C_2$-$C_4$ alkynyl radical, optionally mono-substituted by one of the substituents a) to ac) above;

af) $C_1$-$C_4$ alkyl radical;

ag) $C_1$-$C_4$ alkyl mono-substituted by one of the substituents a)-ac) above;

ah) a 2-oxazolidinonyl moiety in which the point of attachment is the nitrogen atom of the oxazolidinone ring, the ring oxygen atom is optionally replaced by a heteroatom selected from —S— and NR'(where R' is as defined above) and one of the saturated carbon atoms of the oxazolidinone ring is optionally mono-substituted by one of the substituents a) to ag) above; and M is selected from:
i) hydrogen;
ii) a pharmaceutically acceptable esterifying group or removable carboxyl protecting group;
iii) an alkali metal or other pharmaceutically acceptable cation; or
iv) a negative charge which is balanced by a positively charged group.

The present invention also provides novel carbapenem intermediates of the formula:

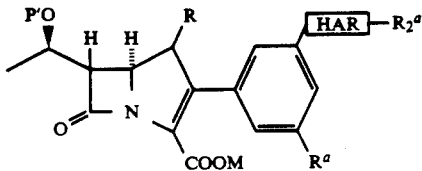

wherein:
R is H or $CH_3$;
$R^a$ is defined above, with the proviso that $R^q$ additionally includes OP' where P' is defined below, that $M^a$ and $M^b$ of $R^q$ both include M and that the Type d) hydroxy substituent additionally may be protected hydroxy, OP';
P' is a removable protecting group for hydroxy;
M is a removable protecting group for carboxy; and the Type I, $R^a$ substituent is counterbalanced with the anionic form of Z where
Z is methanesulfonyloxy, trifluoromethanesulfonyloxy, fluorosulfonyloxy, p-toluenesulfonyloxy, 2,4,6-triisopropylbenzenesulfonyloxy, p-bromobenzenesulfonyloxy, p-nitrobenzenesulfonyloxy, bromo, or iodo.

Preferred intermediates have the formula:

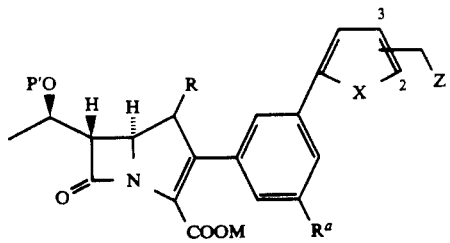

wherein:
R is H or $CH_3$;
P' is a removable protecting group for hydroxy;
M is a removable protecting group for carboxy;
$R^a$ is selected from the group consisting of H, OP', Cl, Br, I, $SCH_3$, CN, CHO, $SOCH_3$, $SO_2CH_3$, $CO_2M$, $CH_2OP'$ or $CONH_2$; and with the proviso that the —$CH_2Z$ substituent is in the 2- or 3-position of the heteroaromatic ring;
X is O or S; and
Z is as defined above.

DETAILED DESCRIPTION OF THE INVENTION

The manufacture of compounds of Formula I may be carried out in a three-stage synthetic scheme followed by deprotection. The objective of the first synthetic stage is to produce a base heteroarylphenyl (hereinafter HAP) compound which may be converted to be the two-position substituent of the carbapenem of Formula I. The objective of the second synthetic stage is to attach the base HAP to the carbapenem. Finally, the objective of the third synthetic stage is to substitute the HAP with the desired $R^a$. This third synthetic stage may either be performed after the first synthetic stage or after the second synthetic stage according to the nature of the desired $R^a$.

Flow Sheet A demonstrates a suggested first stage synthesis. Flow Sheets B1 and B2 demonstrate a second stage synthesis. The third stage synthesis varies according to the selected $R^a$.

FLOW SHEET A

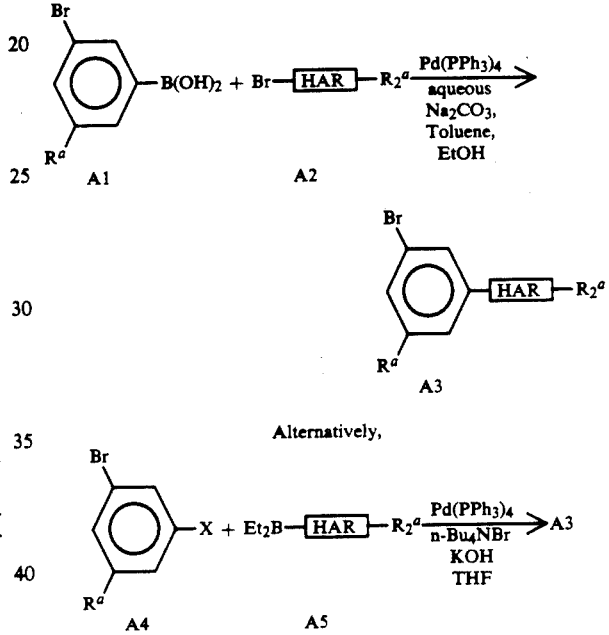

where X = Br, I

Flow Sheet A

Substituted bromophenylboronic acids A1 and substituted heteroaryldiethylboranes A5 may be prepared by conventional methods. Exposure of either of these boron compounds to aryl halides in the presence of a catalytic amount of palladium catalyst yields the desired synthons A3.

Some of these desired synthons A3 may be prepared by the general synthetic routes published in the literature.

Flow Sheet B1

The second stage synthesis is to attach the base HAP to the 2-position of the carbapenem. With compatible $R^a$ or suitable precursor substituents therefor, HAP A3 may be added to azetidin-2-one B1 in a Grignard reaction as shown in Flow Sheet B. (B1 is subgeneric to the more general B1*. Replacing B1 by B1* (where M is as defined above under ii) produces a broader class of compounds analogous to B2, B3, and B4.)

The Grignard reaction requires that A3 be converted to a Grignard reagent by reaction with magnesium and 1,2-dibromoethane in THF from 20° C. to 60° C. and subsequently contacting A3 as a Grignard reagent with B1 in THF at from −70° C. to about 20° C. to produce azetidin-2-one B2. Alternatively, A3 may be reacted with t-butyllithium, n-butyllithium, or the like in Et₂O or THF at from −78° to −50° C. followed by the addition of magnesium bromide to produce the same Grignard reagent. $R^i$ of B1 is in practice pyridin-2-yl but may clearly be a variety of substituents including aromatic and heteroaromatic substituents. Further, $R^i$ might be, for example, phenyl, pyrimidinyl or thiazolyl.

Azetidin-2-one B2 is an intermediate that may be ring closed to a carbapenem. It is on this intermediate that $R^a$ or precursor substituent such as t-butyldimethylsilyloxy-methyl group should be modified where such modification is incompatible with the carbapenem nucleus. For example, a convenient reaction to remove the t-butyldimethylsilyl group from a hydroxymethyl substituent of the HAP on compound B2 is to expose compound B2 to a dilute solution of sulfuric acid or hydrochloric acid in methanol at 0° C. If the t-butyldimethylsilyl group were removed from carbapenem B3 under the same conditions, a substantial portion of carbapenem would be degraded and lost. Thus, modification of the precursor substituent in this instance and replacement with another precursor substituent or even $R^a$ is best performed before closing the carbapenem. Of course it is possible to remove the t-butyldimethylsilyl group from carbapenem B3 in reduced yield by exposing B3 to tetra-n-butylammonium fluoride and acetic acid in THF.

Compound B2 may be ring closed to carbapenem B3 by refluxing in xylene with p-hydroquinone for about 1 to 2 hours. It is on this intermediate that final elaboration of $R^a$ from a precursor substituent, e.g. hydroxymethyl, may be accomplished. Removal of the protecting groups then provides the final compound Formula I. Such final elaboration and deprotection is described in further detail below.

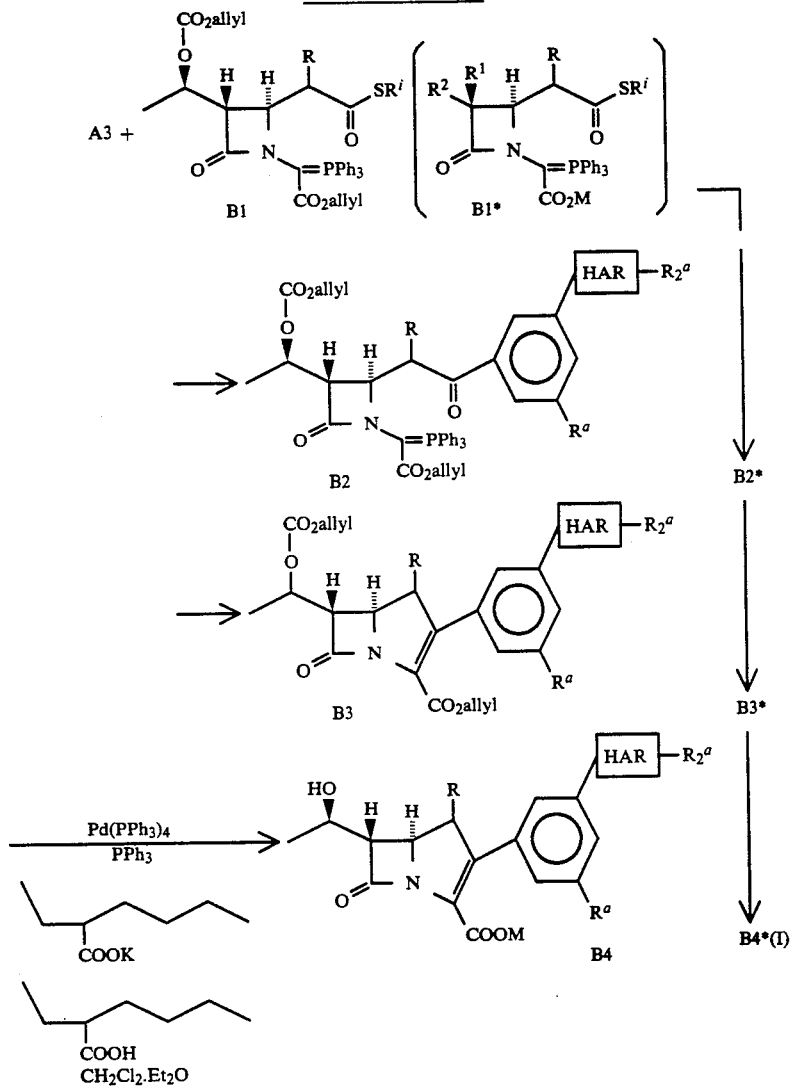

FLOW SHEET B1

Flow Sheet B2

Flow Sheet B2 shows an alternative second stage synthesis, i.e. attachment of the base HAP such as B5 to the 2-position of the carbapenem. This synthesis involves a palladium catalyzed cross-coupling reaction between a carbapenem triflate and a suitably substituted arylstannane, a process which is described in U.S. Ser. No. 650,111 filed Feb. 4, 1991. In order to apply this synthesis, it is first necessary to modify B5 to the trimethylstannylheteroarylphenyl B6. This is accomplished by reacting B5 with t-butyllithium in THF at from −78° to −50° C. followed by the addition of trimethyltin chloride. Alternatively, B6 may be prepared by simply heating B5 with hexamethylditin in the presence of tetrakistriphenylphosphine palladium in toluene solution. At this intermediate stage, it may be desirable to remove certain protecting groups if employed on a precursor substituent $R^a$. For instance, a protecting group such as t-butyldimethylsilyl on a hydroxymethyl substituent may be removed by exposure to tetra-n-butylammonium fluoride in THF yielding a particular B6. If the t-butyldimethylsilyl group were removed from carbapenem B7 under the same conditions, a substantial portion of the carbapenem would be degraded and lost. Thus, modification of the precursor substituent in this instance and replacement with another precursor substituent or even an $R^a$ is best performed before attachment to the carbapenem.

The steps for preparing the 2-oxocarbapenam intermediate B8 are well known in the art and are explained in ample detail by D. G. Melillo et al., *Tetrahedron Letters*, 21, 2783 (1980), T. Salzmann et al., *J. Am. Chem. Soc.*, 102, 6161 (1980), and L. M. Fuentes, I. Shinkai, and T. N. Salzmann, *J. Am. Chem. Soc.*, 108, 4675 (1986). The syntheses are also disclosed in U.S. Pat. Nos. 4,269,772; 4,350,631; 4,383,946; and 4,414,155 all incorporated herein by reference.

Referring again to Flow Sheet B2, the 2-oxocarbapenam, B8, is reacted at −78° C. to −50° C. with a suitable trifluoromethanesulfonyl source, such as trifluoromethanesulfonic anhydride, trifluoromethanesulfonyl chloride and the like, in the presence of an organic nitrogen base, such as triethylamine, diisopropylamine and the like, in a polar aprotic solvent, such as tetrahydrofuran or methylene chloride. Optionally, an organic nitrogen base, such as triethylamine and the like, is then added to the reaction solution followed immediately by a silylating agent, such as trimethylsilyl trifluoromethanesulfonate to provide intermediate B9. An aprotic polar coordinating solvent, such as DMF, 1-methyl-2-pyrrolidinone and the like, is optionally added. This is followed by the addition of a palladium compound, such as tris(dibenzylideneacetone)dipalladium-chloroform (Pd$_2$(DBA)$_3$•CHCl$_3$), palladium acetate and the like, optionally, a suitably substituted phenylphosphine, such as tris(4-methoxyphenyl)phosphine, tris(2,4,6-trimethoxy phenyl)phosphine and the like, and the stannane B6. A halide source such as lithium chloride, zinc chloride or ammonium chloride and the like, is added and the reaction solution is allowed to warm and is stirred at a suitable temperature, such as 0° to 50° C. for from a few minutes to 48 hours. The carbapenem B7 is obtained by conventional isolation/purification methodology known in the art.

Generally speaking, the milder conditions of the synthesis shown in Flow Sheet B2 allow for a wider range of functional group $R^a$ to be present than the synthesis illustrated in Flow Sheet B1. However, in certain cases, it is advantageous for the $R^a$ substituent(s) of the stannane B6 to be introduced in a protected or precursory form. Final elaboration of $R^a$ from a precursor substituent, e.g. hydroxymethyl, may be accomplished on carbapenem intermediate B7. Removal of hydroxyl and ester protecting groups then provides the final compound, C5 of Formula I. Such final elaboration and deprotection is described in detail below.

FLOW SHEET B2

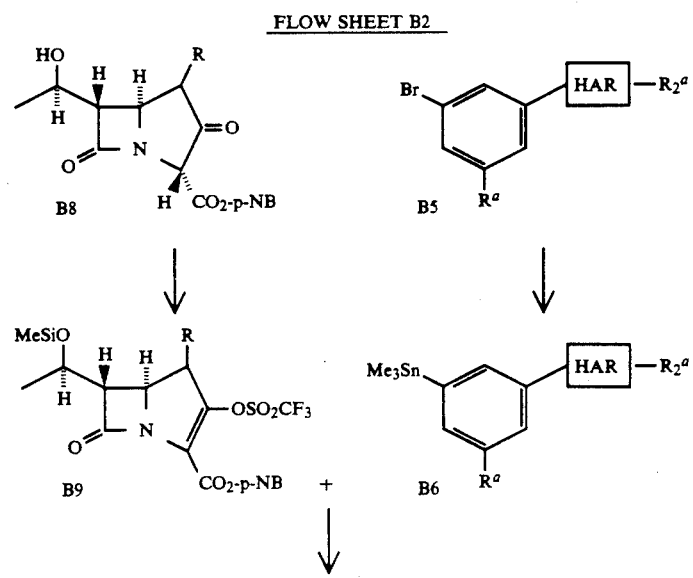

FLOW SHEET B2

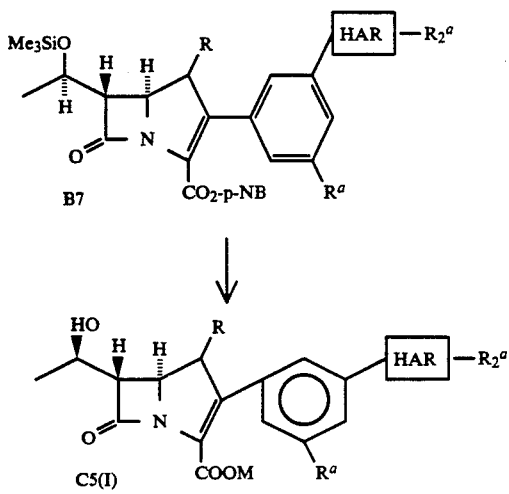

where:

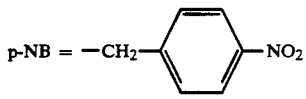

Flow Sheet C

Azetidin-2-ones B1 and B1* (Flow Sheet B1), pyridyl-thioesters, are well known compounds in the production of carbapenems. Diverse synthetic schemes useful to make B1 and B1* may be imagined by the skilled artisan. Particularly useful to the instant inventors is a synthetic scheme set out further in Flow Sheet C below in which the symbol R is as defined above. The steps for preparing intermediate B1 and B1* are analogous to the procedures described, for example, in U.S. Pat. Nos. 4,260,627 and 4,543,257; L. D. Cama et al. *Tetrahedron* 39, 2531 (1983); R. N. Guthikonda et al. *J. Med. Chem.*, 30, 871 (1987) hereby incorporated by reference, as discussed below.

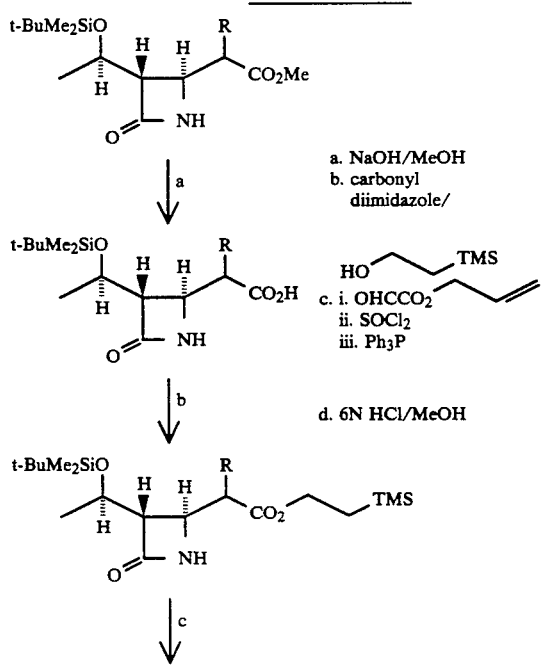

FLOW SHEET C

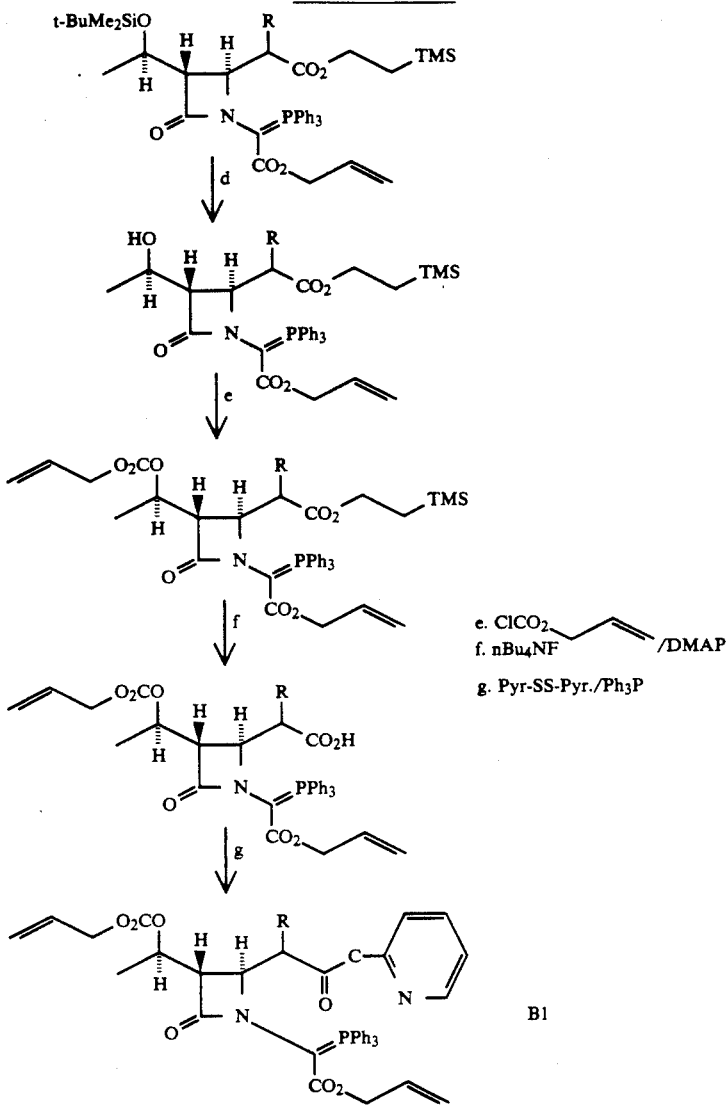

e. $ClCO_2$-CH$_2$CH=CH$_2$
f. $nBu_4NF$ /DMAP
g. Pyr-SS-Pyr./Ph$_3$P

The general synthesis description depicted above in the Flow Sheets shows a protected 1-hydroxyethyl substitution on the 6-position of the carbapenem. After final deprotection, a 1-hydroxyethyl substituent is obtained, which is preferred in most cases. However, it has been found that with certain 2-side-chain selections, the ultimate balance of favorable properties in the overall molecule may be enhanced by selection of the 6-(1-fluoroethyl) moiety instead. Preparation of 6-fluoroalkyl compounds within the scope of the present invention is carried out in a straightforward manner using techniques well known in the art of preparing carbapenem antibacterial compounds. See, e.g., J. G. deVries et al., *Heterocycles*, 23(8), 1915 (1985); BE 900 718 A (Sandoz) and Japanese Patent Pub. No. 6-0163-882-A (Sanruku Ocean).

In the compounds of the present invention, one of the $R^a$ substituents must be of Type I. As a general matter, it is conjectured that anti-MRSA/MRCNS activity results from the configuration of the overall molecule uniquely conferred by the HAP nucleus. The Type I substituent provides still greater anti-MRSA/MRCNS activity to the molecule.

The Type II $R^a$ substituents are distinguishable from Type I substituents chemically and with respect to the biological properties which they confer. In related compounds, it has been found that the Type II substituted compounds afford greater water solubility and reduced potential for CNS side effects. Substituents which tend to confer improved water solubility on the overall compound have been found useful, since they are contemplated to thereby improve the transport of the compound involved. Although a substantial number and range of Type II substituents have been described herein, all of these are contemplated to be a part of the present invention based on the biological performance of substituents related in terms of their medicinal chemistry.

Since it is possible to combine, in the compounds of the present invention, the required Type I substituents with the optional Type II substituents, there can be obtained a combination of desired attributes in the final overall molecule not attainable with a single substituent, i.e., improved anti-MRSA/MRCNS activity together with enhanced water solubility.

Type I substituents employed in the compounds of the present invention may have quaternary nitrogen groups, and these include both cyclic and acyclic types, as is described under Type I. As already pointed out above, it is required that one, but no more than one, of the substituents $R^a$ must be a member selected from the group consisting of the definitions under Type I. It is optional that one, or at most two, of the remaining substituents may be a member selected from the group consisting of definitions under Type II. For example, $R^a$ attached to the phenyl group may be Type I and $R^a$ at a position on the HAR moiety may be of Type II, while the remaining substituents are hydrogen.

In preferred compounds of Formula I, $R^1$ is hydrogen. More preferably, $R^1$ is hydrogen and $R^2$ is (R)—CH₃CH(OH)— or (R)—CH₃CH(F)—. In the most preferred case, $R^1$ is hydrogen and $R^2$ is (R)—CH₃CH(OH)—. While R=H is usually preferred, there are instances in which R=CH₃ may provide improved chemical stability, water solubility, or pharmacokinetic behavior. The substituent R=CH₃ may be of either configuration, i.e., the α or β-stereoisomer. Additionally, in preferred compounds, at least one $R^a$ is other than hydrogen. In the most preferred compounds, in total, up to two $R^a$ substituents are other than hydrogen.

Preferred Type I a) substituents include:

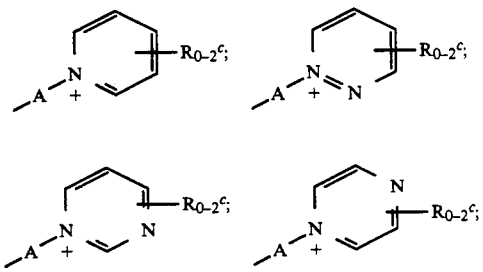

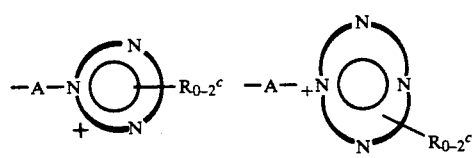

where the ring contains three carbon atoms;

where the ring contains two carbon atoms;

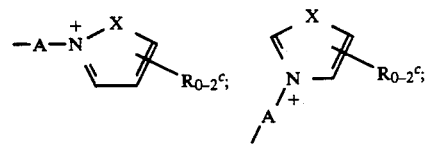

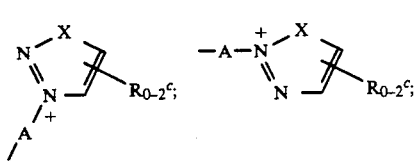

-continued

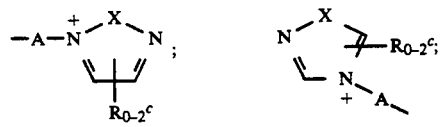

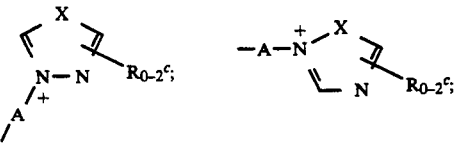

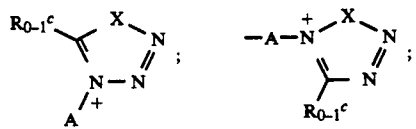

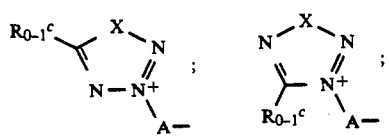

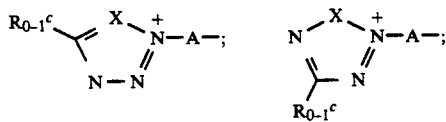

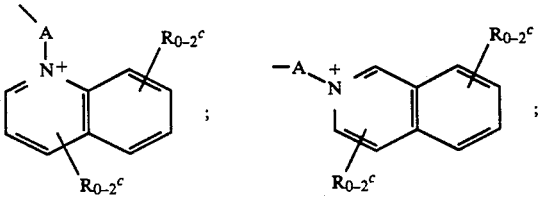

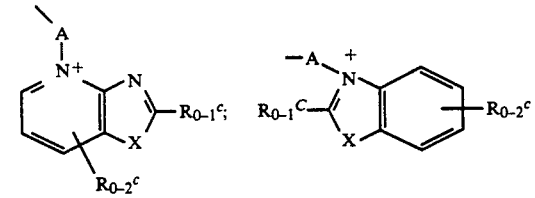

and

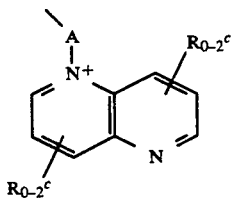

where X=O, S, or NR$^c$. For structures of Type I. a), where R$^c$ is shown to have an indefinite position, it may be attached to any carbon of the ring.

Preferred Type I b) substituents include:

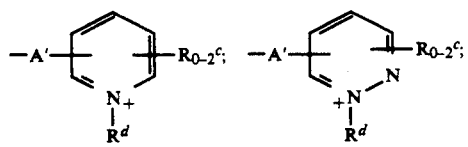
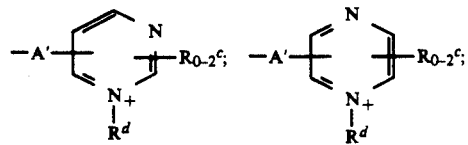
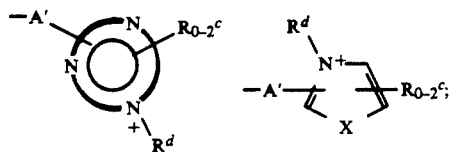

where the ring contains three carbon atoms;

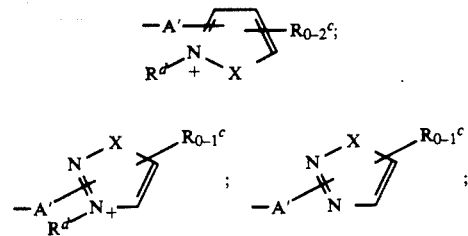
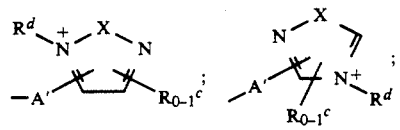
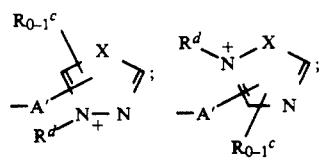
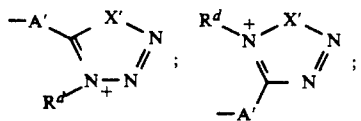
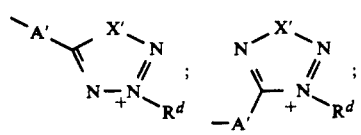
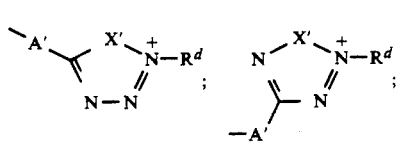

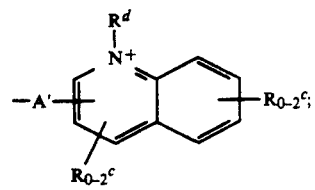
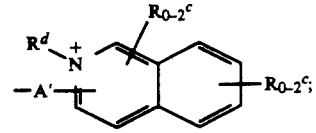
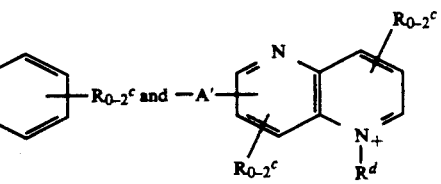

where X=O, S, or NR$^c$ and X'=O or S. For structures of Type I. b), where R$^c$ and/or A' are shown to have indefinite positions, they are independently attached to any carbon atom of the ring.

Preferred Type I c) substituents include: —A$_p$—$^+$N(CH$_3$)$_3$, —A$_p$—$^+$N(CH$_2$CH$_3$)$_3$, —A$_p$—$^+$N(CH$_3$)$_2$CH$_2$R$^q$, —A$_p$—$^+$N(CH$_2$CH$_3$)$_2$CH$_2$CH$_2$R$^q$,

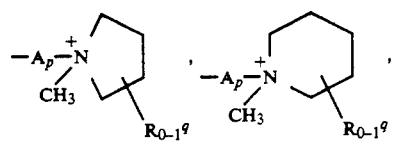
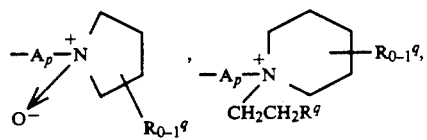
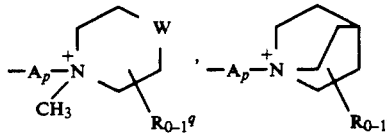
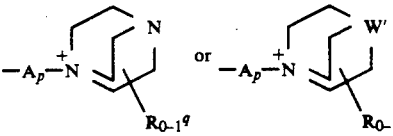

where W is O, S, NR$^e$, N(O)R$^e$, SO, SO$_2$ or N$^+$(R$^e$)$_2$ and W' is N$^+$R$^e$ or NO. For structures of Type I.c), where R$^q$ is shown to have an indefinite position, it may be attached to any carbon atom of the ring.

Preferred Type I
d) substituents include:

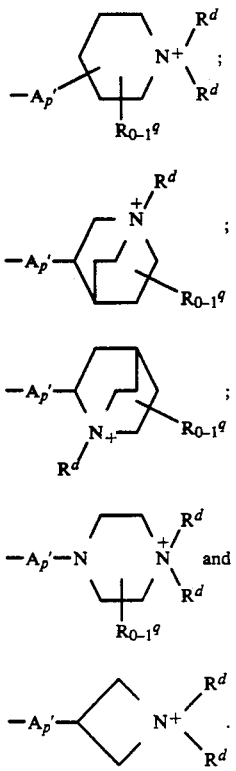

For structures of Type I.d), where $R^q$ and/or $A'_p$ is shown to have an indefinite position, it may be attached to any carbon atom of the ring.

The $R^c$ substituents herein are intended to represent suitable further substituents on the Type I. a) or b) substituents for HAP. As seen above, these Type I. a) or b) substituents are monocyclic or bicyclic aromatic groups containing heteroatoms. Given this class of primary substituent, further suitable substituents may be readily discovered in the penem and carbapenem art. For example, suitable substituents for Type I. a) or b) substituents are generally taught in U.S. Pat. No. 4,729,993 assigned to Merck and Co. or in U.S. Pat. No. 4,746,736 assigned to Bristol-Myers Co. These patents are hereby incorporated by reference.

Broadly, $R^c$ may be the same or different and may be selected on an independent basis from the group as defined above. While a single such substitution is preferred, there is occasion to use up to two such substituents on an $R^a$, e.g., where it is desired to enhance the effect of a particular substituent group by employing multiple substituents. The particular choice of $R^c$ will depend upon the situation. For instance, a specific $R^c$ may lend particular stability to a nitrogen cation. At other times it may be desired to employ a substituent known to enhance antibacterial activity of the overall molecule against a particular bacterium, for example, while also employing a substituent known to improve some other property such as water solubility or the duration of action of the overall molecule.

The scope of $R^c$ herein includes two specific Types of further substituent attached to the Type I. a) or b) substituent. A first Type of $R^c$ are those attached to a ring carbon and a second Type of $R^c$ are those attached to a neutral ring nitrogen. Persons skilled in the art will readily recognize that a wide range of organic substituents are suitably used as $R^c$. Persons skilled in the art will also recognize that some substituents including the $—NR^yR^z$ substituents, useful for one purpose of $R^c$, i.e. carbon substitution, are not equally useful in the other, i.e. nitrogen substitution.

Preferred $R^c$ attached to ring carbon atoms are $—NH_2$, $—SCH_3$, $—SOCH_3$, $—CH_2OH$, $—(CH_2)_2OH$, $—OCH_3$, $—COOM^b$, $—CH_2COOM^b$, $—CH_2CH_2COOM^b$, $—CH_2SOCH_3$, $—CH_2SCH_3$, $CN$, $—SO_3M^b$, $—CH_2SO_3M^b$, $—CH_2CH_2SO_3M^b$, $—Br$, $—Cl$, $—F$, $—I$, $—CH_3$, $CH_2CH_3$, $CH_2CONH_2$ and $CH_2CON(C_1-C_4$ alkyl) where $M^b$ is defined above. Preferred $R^c$ attached to neutral ring nitrogen atoms are $—CH_2OH$, $—(CH_2)_2OH$, $—CH_2COOM^b$, $—CH_2CH_2COOM^b$, $—CH_2SOCH_3$, $—CH_2SCH_3$, $CN$, $—CH_2SO_3M^b$, $—CH_2CH_2SO_3M^b$, $—CH_3$, $CH_2CH_3$, $CH_2CONH_2$ and $CH_2CON(C_1-C_4 alkyl)$ where $M^b$ is defined above.

It is preferred that each Type I. a) or b) substituent have no more than two $R^c$ substituents which are other than hydrogen. Thus, the formula shown above for Type I. a) substituents has up to two $R^c$ substituents with the remainder of course being hydrogen. Further, the formula for the Type I. b) substituent also allows up to two $R^c$. In accordance with these formulae, the previously listed more specific structures should be interpreted to have no more than two $R^c$ for each monocyclic or bicyclic group. Similarly for Type I. c) or d) substituents it is preferred that any monocylic or bicyclic group have no more than a single $R^q$ substituent.

The scope of $R^d$ includes a single type of further substituent attached as a Type I. b) or d) substituent. The $R^d$ substituents are attached to a cationic nitrogen which may or may not be aromatic. Preferred $R^d$ attached to cationic nitrogen atoms are hydrogen, $—CH_3$, $CH_2CH_3$, $—CH_2CH_2CH_3$, $—CH_2COOM^b$, $—CH_2SO_3M^b$, $—NH_2$ and $O^{(-)}$, where $M^b$ is defined above.

The formulas depicting Type Ib, Ic, and Id substituents show positively charged states for those substituents. It is understood that certain of those substituents, which are cationic by virtue of having a protonating hydrogen atom attached to the nitrogen, may also exist or be produced under certain conditions as a neutral substituent by virtue of the absence of such a hydrogen atom (i.e., in Type Ib, when there is no $R^d$; in Type Ic, when there is no $R^w$; and in Type Id, when there is zero to one $R^d$, depending on Type of heterocycle). Whether such a Type Ib, Ic, or Id substituent will be predominately cationic or neutral in a given physical state will be governed by principles of acid-base chemistry, which are well known to those skilled in the art. For example, the particular ratio of neutral form to cationic form will depend upon the basicity of the amine and acidity of a solution. When such a substituent is in a protonated quaternized state, the compound exists as a zwitterion which is internally balanced as to charge or as an ammonium salt which is externally balanced. In illustration, if there is no $R^d$ on a Type Ib substituent, it is understood that such a substituent is neutral (there is no positive charge on the nitrogen). A compound containing such a substituent is typically produced in this form as a salt, wherein M is an alkali metal, and may exist in solution in its neutral form. However, depending upon conditions, a compound containing a neutral Type Ib substituent may be in equilibrium with, and may also be represented by a formula showing, the corresponding compound containing the quaternized protonated substituent where $R^d$ is present and is a hydrogen atom. Furthermore the same compound may exist with the Type Ib substituent in a completely protonated quaternized form, for instance in an aqueous solution in the presence of a stoichiometric amount of a strong mineral acid. It is intended herein that both the protonated (cationic) and the unprotonated (neutral) forms of Type Ib, Ic and Id substituents of the type just described are within the scope of the present invention.

Suitable A spacer moieties include —$CH_2$—, —$CH_2CH_2$—, —$CH_2CH_2CH_2$—, —$CH_2CH_2CH_2CH_2$—, —$OCH_2CH_2$—, —$SOCH_2$—, —$SO_2CH_2$—, —$SCH_2CH_2$—, —$SOCH_2CH_2$—, —$SO_2CH_2CH_2$—, —$NHCH_2CH_2$—, —$N(CH_3)CH_2CH_2$—, —$CH_2N(CH_3)CH_2CH_2$—, —$CONHCH_2CH_2$—, —$SO_2NHCH_2CH_2$—, —$COCH_2$—, —$CH=CHCH_2$— and —$CH_2OCH_2CH_2$—. Preferably, where Q is O, S, NH or $N(C_{1-4}alkyl)$, then n is 2–6.

Suitable A' are listed for A above. Further A' may suitably be —O—, —S—, —NH—, —$SO_2$—, —$SO_2NH$—, —CONH—, —CH=CH—, —$CH_2S$—, —$CH_2NH$—, —$CONHCH_2$— or —$SO_2NHCH_2$—.

The Type I. cationic substituents are generally added to HAP following attachment of HAP to the carbapenem. Conveniently, the HAP side-chain should be synthesized with a precursor substituent which may be elaborated into the desired cationic substituent. The identity of the precursor substituent will vary according to the particular $R^a$ desired. For example, one such precursor substituent is —A—OH, such as hydroxymethyl.

The hydroxymethyl precursor substituent may be elaborated into cationic substituents of Type I.a) by converting the hydroxyl into an active leaving group such as an iodide (giving —A—I) followed by reaction with a desired nitrogen containing aromatic compound. More particularly, two alternative procedures may be utilized to produce a leaving group on the moiety —A— and subsequently to replace such a leaving group with cationic substituents of the type just described.

For a first procedure, the hydroxyl group of —A—OH may be converted to a methanesulfonate group by treating with methanesulfonyl chloride in the presence of triethylamine. A suitable solvent, e.g., dichloromethane, is employed and the reaction is carried out at reduced temperatures. In turn, the methanesulfonate intermediate may be converted to the reactive iodide derivative by treatment with sodium iodide in a suitable solvent, e.g., acetone, at reduced or ambient temperatures. Alternatively, the hydroxyl group may be directly converted into the iodide group by common methods known to the art. For example, treatment of the hydroxyl group with methyl triphenoxyphosphonium iodide in a suitable solvent, such as dimethylformamide, at reduced or ambient temperatures, directly provides the desired iodide. Once the iodide has been formed, the introduction of the cationic substituent is accomplished simply by treating the iodide with the desired nitrogen containing compound, e.g. a heteroaromatic compound such as pyridine. The reaction will proceed in a suitable solvent, such as acetonitrile, at or about room temperature. This displacement reaction may also be facilitated by the addition of excess silver trifluoromethanesulfonate to the reaction mixture, in which case reduced temperatures are often desirable.

For a second procedure, the hydroxyl group of —A—OH may be converted into the reactive trifluoromethanesulfonate (triflate) group. However, such an activating group cannot be isolated by conventional techniques but may be formed and used in situ. Thus, treatment of the hydroxyl group with trifluoromethanesulfonic (triflic) anhydride in the presence of a hindered, non-nucleophilic base such as 2,6-lutidine, 2,4,6-collidine, or 2,6-di-tert-butyl-4-methylpyridine in a suitable solvent, such as dichloromethane, at reduced temperatures provides for the generation of the triflate activating group. Introduction of the cationic group is then accomplished by reacting the above triflate in situ with the desired nitrogen containing compound at reduced temperature. In certain cases it is possible and desirable to use the reacting nitrogen containing compound as the base for the formation of the triflate activating group. In this case treatment of the hydroxyl group with triflic anhydride in the presence of at least two equivalents of the reacting nitrogen compound under the conditions described above provides the cationic substituent.

The above are representative of suitable leaving groups: alkylsulfonyloxy, substituted alkylsulfonyloxy, arylsulfonyloxy, substituted arylsulfonyloxy, fluorosulfonyloxy and halogen. The common sulfonate leaving groups are: methanesulfonyloxy, trifluoromethanesulfonyloxy, fluorosulfonyloxy, p-toluenesulfonyloxy, 2,4,6-tri-isopropylbenzenesulfonyloxy, p-bromobenzenesulfonyloxy and p-nitrobenzenesulfonyloxy. The preferred halo leaving groups are bromo and iodo. These alkyl and arylsulfonate leaving groups may be prepared using an analogous route to the one described above using the sulfonyl chloride or the sulfonic anhydride.

Where the cationic substitution has a substituent $R^c$, the most facile method of providing such a substituent is to employ as the reactant in the preparation methods described above a nitrogen containing compound which already has the desired substituent. Such substituted compounds are readily available starting materials or may be prepared in a straight-forward manner using known literature methods.

The Type I.b) cationic substituents are prepared by quaternization of an aromatic ring nitrogen of a neutral precursor substituent on either of the HAP rings. Examples of neutral precursor substituents are —$CONHCH_2$-(2-pyridyl), —$CONHCH_2$-(4-pyridyl) or —$SO_2CH_2$-(4-pyridyl). Quaternization is accomplished by reacting the nitrogen compound in an inert organic solvent (e.g.$CH_2Cl_2$) at about 0° C. to room temperature with an alkylating agent $R^d$-Y where $R^d$ is given above and Y is a leaving group such as iodide, bromide, mesylate (methanesulfonate), tosylate (p-toluenesulfonate) or triflate. Alternatively, the aromatic ring nitrogen may be quaternized by reaction with an oxidizing agent such as 3-chloroperbenzoic acid (giving the N-oxide) or an aminating reagent such as O-(2,4,6-triisopropylbenzenesulfonyl)hydroxylamine (giving the N-amino derivative) in a suitable solvent (e.g. dichloromethane or $CH_3CN$) at about room temperature. In addition, the neutral precursor substituent may be rendered cationic through protonation of the basic aromatic ring nitrogen. This may be accomplished by treatment of the neutral precursor with a suitable inorganic or organic acid, e.g. hydrochloric acid, phosphoric acid, hydrobromic acid, acetic acid or benzoic acid. Protonation may further be accomplished by a carboxylic acid function elsewhere in the molecule, including the C-3 carboxyl on the carbapenem. The neutral precursor substituent may be already attached to HAP at the time of its connection to the carbapenem, or it may be elaborated from a simpler precursor after connection to the carbapenem. An example of a precursor substituent for elaboration is —A'—OH such as hydroxymethyl. In one suggested synthesis, the hydroxyl may be converted to a reactive leaving group such as iodo as described above. The iodide is then reacted in a nucleophilic displacement reaction with a nitrogen containing aromatic compound which has a nucleophilic side-chain substituent such as $CH_2SH$ or $CH_2NH_2$. In this displacement reaction, it is the side-chain substituent that is the reacting nucleophile and not the aromatic ring nitrogen. Suitable substrates for this reaction include 2-(mercaptomethyl)-pyridine, 2-aminopyridine, 2-(aminomethyl)pyridine or 4-(mercaptomethyl)pyridine. The reaction is carried-out in an inert organic solvent, e.g. methylene chloride, at from about 0° C. to room temperature in the presence of a non-nucleophilic base such as triethylamine or diisopropylethylamine. Quaternization or protonation of the aromatic ring nitrogen as described above then gives the Type I.b) cationic substituent. A second suggested synthesis of a Type I.b) cationic substituent starting from a precursor —A'—OH (e.g. hydroxymethyl) consists of oxidation of the alcohol functionallity to an aldehyde followed by Wittig-type olefination with an appropriate nitrogen-containing aromatic substituted reagent, and finally quaternization. The oxidation may be conveniently accomplished by a Swern oxidation employing oxalyl chloride-dimethylsulfoxide followed by triethylamine. The reaction is conducted in methylene chloride as a solvent at from −70° C. to 0° C. The Wittig reaction is carried-out by reacting the aldehyde with the desired Wittig reagent in a polar solvent such as acetonitrile or dimethylsulfoxide at about room temperature. Suitable Wittig reagents include: pyridylmethylenetriphenylphosphorane, quinolylmethylenetriphenylphosphorane, and thiazolylmethylenetriphenylphosphorane. Quaternization or protonation as described above then completes the synthesis of the Type I.b) cationic substituent. Depending on the particular $R^a$ of Type I.b) that is desired, many other synthesis schemes may be employed, as would be apparent to an organic chemist skilled in the art.

The Type I.c) cationic substituents may be prepared in an analogous manner to that described for I.a) substituents except that the nitrogen containing compound employed in the displacement reaction is an aliphatic amine (i.e. $NR^yR^zR^w$). However, in cases where the amino group is directly bonded to HAP (i.e. —$A_p$N-+$R^yR^zR^w$ where p=0), the amine is most conveniently attached to HAP prior to its incorporation into the carbapenem system. If such an amine is primary or secondary, it may require protection with a suitable amine protecting group during the steps employed to attach HAP to the carbapenem. Tertiary amines require no protection and may be quaternized or protonated as described for the Type I.b) cationic substituents.

The Type I.d) cationic substituents are prepared by quaternization or protonation of a non-aromatic ring nitrogen of an appropriate neutral precursor substituent on HAP. Quaternization or protonation is accomplished as described above for the Type I.b) substituents. As with the Type I.b) substituents, the neutral precursor may already be attached to HAP at the time of its connection to the carbapenem, or the neutral precursor may be elaborated from a simpler precursor substituent on HAP after its connection to the carbapenem. Examples of neutral precursor substituents are: —CONH(3-quinuclidinyl), —CONH[4-(N-methylpiperidinyl)], —$SO_2CH_2CH_2$[2-(N-methylpyrrolidinyl)], —$SO_2NH$[1-(4-methylpiperazinyl)] and —$CH_2$[1-(4-methylpiperazinyl)]. Elaboration of the neutral precursor substituent from a simpler substituent such as hydroxymethyl may be accomplished in an analogous manner to that described previously for the Type I.b) substituents by employing appropriate reagents to introduce the Type I.d) non-aromatic ring nitrogen moiety which is subsequently to be quaternized or protonated.

It should be clear that for any of the Type I.a) to I.d) substituents, the substituent may be suitably formed on HAP prior to addition to the carbapenem. Thus, the substituent may be formed on B6 and reacted with B9 to form the protected carbapenem B7. For example, 2-hydroxymethyl-5-(3'-trimethylstannylphenyl)thiophene, i.e. B6, may be substituted by reaction with triflic anhydride and N-methylimidazole in a suitable solvent, such as, dichloromethane under nitrogen at −78° C. to room temperature to form a Type I.a) substituted HAP, i.e. B6. This substituted HAP may be reacted with B9 employing conditions otherwise described herein and specifically using an ammonium chloride source.

In the compounds of the present invention, the $R^a$ substituents can be selected based on the biological properties which they confer. In related compounds, it has been found that the neutral or anionic substituted compounds afford greater water solubility and reduced potential for CNS side effects. Substituents which tend to confer improved water solubility on the overall compound have been found useful, since they are contemplated to thereby improve the transport of the compound involved. Although a substantial number and range of substituents have been described herein, all of these are contemplated to be a part of the present invention based on the biological performance of substituents related in terms of their medicinal chemistry.

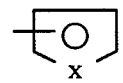

is a 5-, 8-, or 9-membered mono- or bicyclic aromatic ring system wherein up to two carbon atoms are replaced by O or S. HAR can be represented by

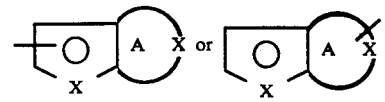

5-membered aromatic ring wherein one carbon atom is replaced by O or S).

Thus, this aryl structure may be the radical of a 5-membered furan or thiophene, of an 8-membered furofuran, thienofuran, or thienothiophene, or of a 9-membered benzofuran or benzothiophene. The carbon atom at the point of attachment, however, cannot be replaced by a heteroatom.

The $R^a$ substituents are on the carbon atoms of the aryl ring system but not on the one at the point of attachment. It is preferred that $R^a = H$ when it is $\alpha$ to the point of attachment.

In preferred compounds of Formula I, $R^1$ is hydrogen. More preferably, $R^1$ is hydrogen and $R^2$ is (R)—CH$_3$CH(OH)— or (R)—CH$_3$CH(F)—. In the most preferred case, $R^1$ is H and $R^2$ is (R)—CH$_3$CH(OH). While R=H is usually preferred, there are instances in which R=CH$_3$ may provide improved chemical stability, water solubility, or pharmacokinetic behavior. The substituent R=CH$_3$ may be of either configuration, i.e., the $\alpha$ or $\beta$-stereoisomer. Additionally, in preferred compounds, at least one $R^a$ in the meta-position of the HAP moiety from the point of attachment to the other aromatic ring is other than hydrogen. In the most preferred compounds, in total, up to two $R^a$ substituents are other than hydrogen.

Among preferred $R^a$ substituents are C$_1$–C$_4$ alkyl mono-substituted with hydroxy, such as, hydroxymethyl; formyl; carbamoyl, such as, —CONH$_2$; hydroxyiminomethyl, such as, —CH=NOH; cyano; or halogen such as chloro, bromo, and iodo.

Flow Sheet D

In regard to this preferred substitution, the hydroxymethyl group may be obtained in the $R^a$ position of the phenyl portion of HAP as shown in Flow Sheet D, in which A3 is obtained as given in Flow Sheet A. Selective metallation of A3 and formylation with N,N-dimethylformamide provides synthon D1. Reduction of D1 with sodium borohydride in methanol yields the preferred substituent which is protected as its silylether in the next step to give D3. The latter reagent is then incorporated into Flow Sheet B1 as A3. The preferred hydroxymethyl group may also be obtained in the appropriate $R^a$ positions of the heteroaryl portion of HAP. Thus, by a judicious choice of starting materials as exhibited in Flow Sheet A, the desired substitution pattern is readily available.

FLOW SHEET D

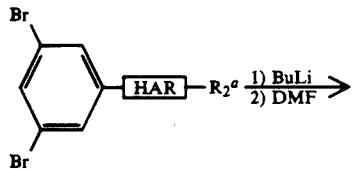

A3(phenyl $R^a$ = Br)

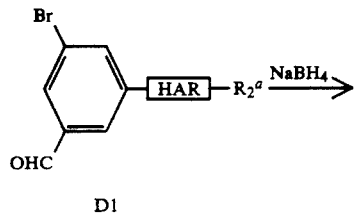

D1

-continued
FLOW SHEET D

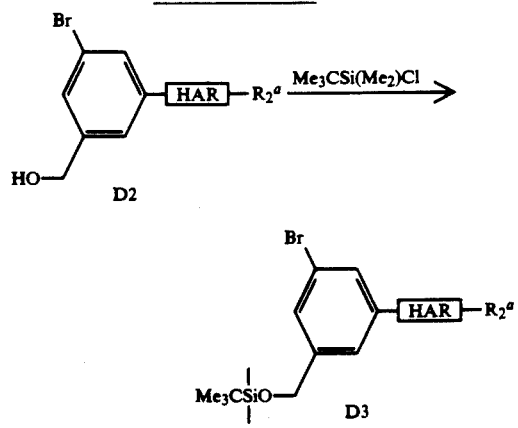

The preferred formyl substitution on the HAP moiety may be obtained from the hydroxymethyl substitution of B3 or isomeric B3* described in Flow Sheet B1 by a Swern oxidation. For example, isomeric B3* is oxidized in methylene chloride at from −70° C. to room temperature employing oxalyl chloride-dimethyl sulfoxide as the active agent. Obviously, the position of the resultant formyl substitution will depend upon the position of the hydroxymethyl substitution in isomeric B3*.

The preferred —CH=NOH substitution on the HAP moiety may be conveniently obtained from the formyl substitution just described. This is accomplished simply by exposing the formyl substituted compound to hydroxylamine in an appropriate solvent at room temperature.

The preferred cyano substitution on the HAP moiety may be obtained from the —CH=NOH substitution just described. The —CH=NOH substituted compound is dehydrated with triflic anhydride and triethylamine in a solvent at −70° C.

The preferred carbamoyl substitution, —CONH$_2$, may be obtained from B2 or "isomeric" B2* by oxidizing hydroxymethyl with Jones reagent to the corresponding carboxylic acid substitution as described above. This carboxylic acid is converted to —CONH$_2$ by sequentially contacting with 1-ethyl-3-(3-dimethylaminopropyl)carbodiimide hydrochloride, 1-hydroxybenzotriazole, and ammonia in an organic solvent at room temperature. Substituted amides may of course be obtained by replacing ammonia with the corresponding substituted amine. In contrast to the carboxylic acid substitution, this carbamoyl substituent requires no protection from the conditions of carbapenem cyclization. Deprotection following cyclization is carried out with palladium catalyzed deallylation in a solution containing potassium or sodium 2-ethylhexanoate as described in McCombie and Jeffrey, *J. Org. Chem.*, 47, 2505 (1983). Deprotection in such a solution yields the desired potassium or sodium salt.

In addition to or including the above, suitable $R^a$ of Type II include:

-OCH$_3$
-OCH$_2$CH$_2$OH      -OCH$_2$CO$_2$CH$_3$
-F                    -CF$_3$
-Br                   -Cl
-OH                   -I

| -continued | |
|---|---|
| -OCONH$_2$ | -OCOCH$_3$ |
| -SOCH$_3$ | -SCH$_3$ |
| -SCH$_2$CH$_2$OH | -SO$_2$CH$_3$ |
| -SO$_2$NH$_2$ | -SOCH$_2$CH$_2$OH |
| -NHCHO | -SO$_2$N(CH$_3$)$_2$ |
| -NHCO$_2$CH$_3$ | -NHCOCH$_3$ |
| -CN | -NHSO$_2$CH$_3$ |
| -COCH$_3$ | -CHO |
| -CH=NOH | -COCH$_2$OH |
| -CH=NOCH$_2$CO$_2$CH$_3$ | -CH=NOCH$_3$ |
| -SO$_2$CH$_2$CH$_2$OH | -CH=NOCMe$_2$CONH$_2$ |
| -CH=NOCMe$_2$CO$_2$Me | -CO$_2$CH$_2$CH$_2$OH |
| -CONH$_2$ | -CONHCH$_3$ |
| -CON(CH$_3$)$_2$ | -CONHCH$_2$CN |
| -CONHCH$_2$CONH$_2$ | -CONHCH$_2$CO$_2$CH$_3$ |
| -CONHOH | -CONHCH$_3$ |
| -tetrazolyl | -CO$_2$CH$_3$ |
| -SCF$_3$ | -CONHSO$_2$NH$_2$ |
| -CONHSO$_2$NH$_2$ | -SO$_2$NHCN |
| -SO$_2$CF$_3$ | -CH=CHCN |
| -SO$_2$NHCONH$_2$ | -CH=CHCO$_2$CH$_3$ |
| -CH=CHCONH$_2$ | -C≡C-CN |
| -C≡C-CONH$_2$ | -CH$_2$N$_3$ and |
| -CH$_2$OH | -CH$_2$I. |
| -CH$_2$CO$_2$CH$_3$ | |

In the preparation methods described above, the carboxyl group at the 3-position and the hydroxyl group at the 8-position of the carbapenem remain blocked by protecting groups until the final product is prepared. Suitable hydroxyl protecting groups, P', are silyl groups such as trialkylsilyl, aryl(alkyl)alkoxysilyl, alkoxydiarylsilyl and diarylalkylsilyl and carbonate groups such as alkyloxycarbonyl, substituted alkyloxycarbonyl, benzyloxycarbonyl, substituted benzyloxycarbonyl, allyloxycarbonyl and substituted allyloxycarbonyl. The preferred protecting groups, in addition to or including those shown in the schemes, are t-butylmethoxyphenylsilyl, t-butoxydiphenylsilyl, trimethylsilyl, triethylsilyl, t-butyldimethylsilyl, o-nitrobenzyloxycarbonyl, p-nitrobenzyloxycarbonyl, benzyloxycarbonyl, t-butyloxycarbonyl, 2,2,2-trichloroethyloxycarbonyl and allyloxycarbonyl. Suitable carboxyl protecting groups, M, in addition to or including those shown in the schemes are described herein below.

Deblocking may be carried out in a conventional manner, with care being taken to avoid a procedure which is so harsh as to disrupt other portions of the final product molecule. For compounds prepared according to Flow Sheet B1, deprotection may be carried out in a palladium catalyzed reaction in a solution containing potassium 2-ethylhexanoate and 2-ethylhexanoic acid or, alternatively, another suitable nucleophile such as pyrrolidine. Alternatively, for those prepared via Flow Sheet B2, deprotection is conducted sequentially. Thus, compound B7 is exposed initially to aqueous acidic conditions, acetic acid or dilute HCl or the like, in an organic solvent such as tetrahydrofuran at 0° C. to ambient temperature for from a few minutes to several hours. The resulting desilylated carbapenem may be isolated by conventional techniques, but is more conveniently taken into the final deprotection process. Thus, addition of an inorganic base such as NaHCO$_3$ or KHCO$_3$ and a catalyst, such as, 10% Pd/C or 5% Rh/Al$_2$O$_3$ followed by hydrogenation provides for the removal of the p-nitrobenzyl protecting group and the formation of the final compound of Formula I.

The overall molecule must be electronically balanced. Since a quaternary nitrogen is present in the compounds of the present invention, a balancing anion must also, in that case, be present. This is usually accomplished by allowing COOM to be COO$^-$. However, where M is, e.g., a pharmaceutically acceptable ester, a counterion (anion) Z$^-$ must be provided, or alternatively, an anionic substituent might be utilized. A counterion must also be provided or additional anionic substituent utilized where there is more than one quaternary nitrogen. Further, it is within the scope of this invention to utilize an anionic substituent where the quaternary nitrogen is already balanced by COOM=-COO$^-$. In that case, it will be understood that it is necessary to provide a counterion (cation) for the anionic substituent. However, it is well within the skill of a medicinal chemist, to whom there is available many suitable anionic and cationic counterions, to make such choices.

With reference to the above definitions, "alkyl" means a straight or branched chain aliphatic hydrocarbon radical.

The term "quaternary nitrogen" as used herein refers to a tetravalent cationic nitrogen atom including the cationic nitrogen atom in a tetra-alkylammonium group (e.g., tetramethylammonium, N-methylpyridinium), the cationic nitrogen atom in a protonated ammonium species (e.g., trimethylhydroammonium, N-hydropyridinium), the cationic nitrogen atom in an amine N-oxide (e.g., N-methylmorpholine-N-oxide, pyridine-N-oxide), and the cationic nitrogen atom in an N-amino-ammonium group (e.g., N-aminopyridinium).

The term "heteroatom" means N, S, or O, selected on an independent basis.

The term "heteroaryl" has been defined herein, in relation to the R$^x$ group, to have a specific and limited meaning, being only monocyclic. It is required that the monocyclic heteroaryl have at least one nitrogen atom, and optionally at most only one additional oxygen or sulfur heteroatom may be present. Heteroaryls of this type are pyrrole and pyridine (1N); and oxazole, thiazole or oxazine (1N+1 O or 1 S). While additional nitrogen atoms may be present together with the first nitrogen and oxygen or sulfur, giving, e.g., a thiadiazole (2N's+1 S), the preferred heteroaryls are those where only nitrogen heteroatoms are present when there is more than one. Typical of these are pyrazole, imidazole, pyrimidine and pyrazine (2N's) and triazine (3N's).

The heteroaryl group of R$^x$ is always optionally mono-substituted by R$^q$, defined above, and substitution can be on one of the carbon atoms or one of the heteroatoms, although in the latter case certain substitutent choices may not be appropriate.

Listed in Table I are specific compounds of the instant invention. In the table, R$^2$ substituents containing a chiral center (i.e., —CH(F)CH$_3$ and —CH(OH)CH$_3$) have the (R) configuration, and the R$^a$ column refers to the substituent on the phenyl ring.

TABLE I

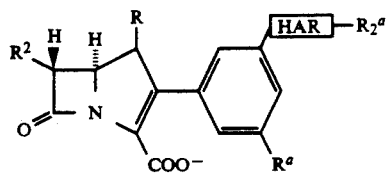

| No. | R | R² | Rᵃ | HAR-R₂ᵃ |
|---|---|---|---|---|
| 1 | H | —CH(OH)CH₃ | H | thiophene-CH₂-N⁺(imidazole)NCH₃ |
| 2 | H | —CH(OH)CH₃ | Cl | thiophene-CH₂-N⁺(imidazole)NCH₃ |
| 3 | H | —CH(OH)CH₃ | Br | thiophene-CH₂-N⁺(imidazole)NCH₃ |
| 4 | H | —CH(OH)CH₃ | I | thiophene-CH₂-N⁺(imidazole)NCH₃ |
| 5 | H | —CH(OH)CH₃ | SMe | thiophene-CH₂-N⁺(imidazole)NCH₃ |
| 6 | H | —CH(OH)CH₃ | S(O)Me | thiophene-CH₂-N⁺(imidazole)NCH₃ |
| 7 | H | —CH(OH)CH₃ | SO₂Me | thiophene-CH₂-N⁺(imidazole)NCH₃ |
| 8 | H | —CH(OH)CH₃ | F | thiophene-CH₂-N⁺(imidazole)NCH₃ |
| 9 | H | —CH(OH)CH₃ | H | thiophene(3-substituted)-CH₂-N⁺(imidazole)NCH₃ |
| 10 | H | —CH(OH)CH₃ | H | thiophene-CH₂-N⁺(imidazole)NCH₃ |
| 11 | H | —CH(OH)CH₃ | F | thiophene(3-substituted)-CH₂-N⁺(imidazole)NCH₃ |
| 12 | H | —CH(OH)CH₃ | F | thiophene-CH₂-N⁺(imidazole)NCH₃ |

TABLE I-continued
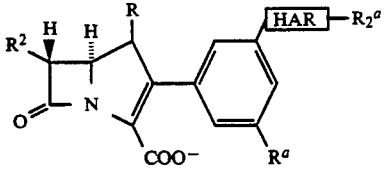
| No. | R | R² | Rᵃ | HAR-R₂ᵃ | |
|---|---|---|---|---|---|
| 13 | H | —CH(OH)CH₃ | Br | 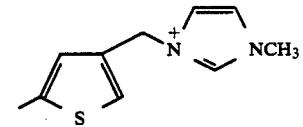 | |
| 14 | H | —CH(OH)CH₃ | Br | 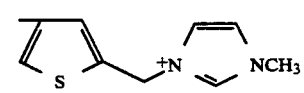 | |
| 15 | H | —CH(OH)CH₃ | I | 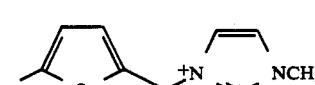 | |
| 16 | H | —CH(OH)CH₃ | I | 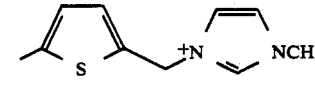 | |
| 17 | H | —CH(OH)CH₃ | Cl | 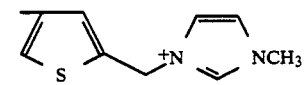 | |
| 18 | H | —CH(OH)CH₃ | Cl | 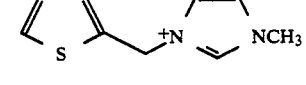 | |
| 19 | H | —CH(OH)CH₃ | 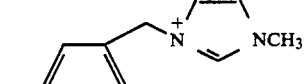 | 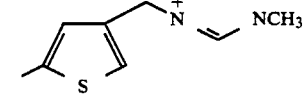 | |
| 20 | H | —CH(OH)CH₃ | 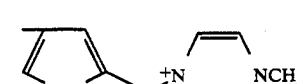 | 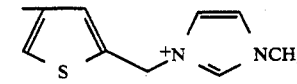 | |
| 21 | H | —CH(OH)CH₃ |  | 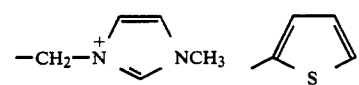 | |
| 22 | H | —CH(OH)CH₃ |  | 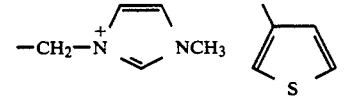 | |
| 23 | H | —CH(OH)CH₃ | 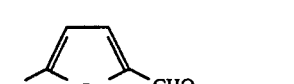 | 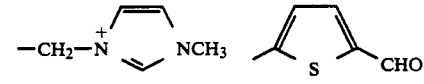 | |
| 24 | H | —CH(OH)CH₃ | —CHO | 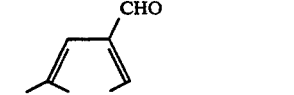 | |

TABLE I-continued

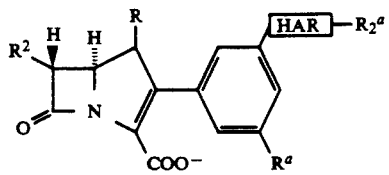

| No. | R | R² | Rᵃ | HAR-R₂ᵃ |
|---|---|---|---|---|
| 25 | H | —CH(OH)CH₃ | —CN | (5-methylthiophene-CH₂-N⁺-imidazole-NCH₃) |
| 26 | H | —CH(OH)CH₃ | —C(O)NH₂ | (5-methylthiophene-CH₂-N⁺-imidazole-NCH₃) |
| 27 | H | —CH(OH)CH₃ | —CHO | (5-methylthiophene-CH₂-N⁺=CH-CH=CH-NCH₃) |
| 28 | H | —CH(OH)CH₃ | —CN | (5-methylthiophene-CH₂-N⁺=CH-CH=CH-NCH₃) |
| 29 | H | —CH(OH)CH₃ | —C(O)NH₂ | (5-methylthiophene-CH₂-N⁺=CH-CH=CH-NCH₃) |
| 30 | H | —CH(OH)CH₃ | H | (5-methylthiophene-CH₂-N⁺-pyridine-3-NH₂) |
| 31 | H | —CH(OH)CH₃ | H | (5-methylthiophene-CH₂-N⁺-pyridine-4-NH₂) |
| 32 | H | —CH(OH)CH₃ | H | (5-methylthiophene-CH₂-N⁺-pyridine-3-CH₂SCH₃) |
| 33 | H | —CH(OH)CH₃ | —SCH₃ | (5-methylthiophene-CH₂-N⁺=CH-CH=CH-NCH₃) |
| 34 | H | —CH(OH)CH₃ | —S(O)CH₃ | (5-methylthiophene-CH₂-N⁺=CH-CH=CH-NCH₃) |
| 35 | H | —CH(OH)CH₃ | —SO₂CH₃ | (5-methylthiophene-CH₂-N⁺=CH-CH=CH-NCH₃) |
| 36 | H | —CH(OH)CH₃ | —SCH₃ | (thiophene-CH₂-N⁺-imidazole-NCH₃) |

TABLE I-continued

I'

| No. | R | R² | Rᵃ | HAR-R₂ᵃ |
|-----|---|-----|-----|---------|
| 37 | H | —CH(OH)CH₃ | —S(=O)CH₃ | thienyl-CH₂-N⁺(imidazole)-NCH₃ |
| 38 | H | —CH(OH)CH₃ | —S(=O)₂CH₃ | thienyl-CH₂-N⁺(imidazole)-NCH₃ |
| 39 | H | —CH(OH)CH₃ | H | 5-methylthienyl-CH₂-N⁺(pyridyl)-NH₂ |
| 40 | H | —CH(OH)CH₃ | F | 5-methylthienyl-CH₂-N⁺(pyridyl)-NH₂ |
| 41 | H | —CH(OH)CH₃ | Cl | 5-methylthienyl-CH₂-N⁺(pyridyl)-NH₂ |
| 42 | H | —CH(OH)CH₃ | Br | 5-methylthienyl-CH₂-N⁺(pyridyl)-NH₂ |
| 43 | H | —CH(OH)CH₃ | I | 5-methylthienyl-CH₂-N⁺(pyridyl)-NH₂ |
| 44 | H | —CH(OH)CH₃ | —SCH₃ | 5-methylthienyl-CH₂-N⁺(pyridyl)-NH₂ |
| 45 | H | —CH(OH)CH₃ | —S(=O)CH₃ | 5-methylthienyl-CH₂-N⁺(pyridyl)-NH₂ |

TABLE I-continued
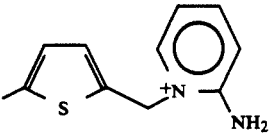
| No. | R | $R^2$ | $R^a$ | HAR-$R_2{}^a$ |
|---|---|---|---|---|
| 46 | H | —CH(OH)CH$_3$ | $-\overset{O}{\underset{O}{S}}CH_3$ | 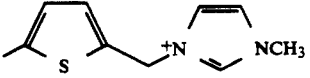 |
| 47 | CH$_3$ | —CH(OH)CH$_3$ | H | 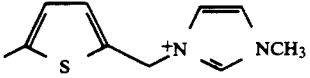 |
| 48 | H | —CH(F)CH$_3$ | H | 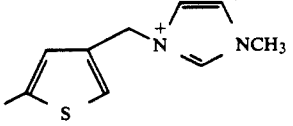 |
| 49 | H | —CH(F)CH$_3$ | H | 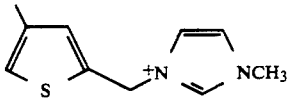 |
| 50 | H | —CH(F)CH$_3$ | H | 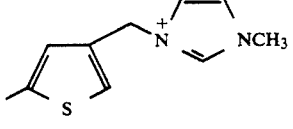 |
| 51 | CH$_3$ | —CH(OH)CH$_3$ | H | 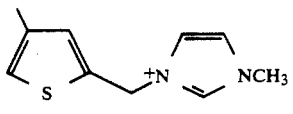 |
| 52 | CH$_3$ | —CH(OH)CH$_3$ | H | 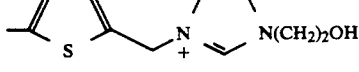 |
| 53 | H | —CH(OH)CH$_3$ | CN | 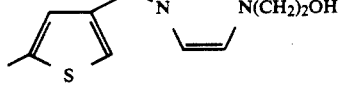 |
| 54 | H | —CH(OH)CH$_3$ | CN | 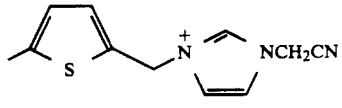 |
| 55 | H | —CH(OH)CH$_3$ | CN | 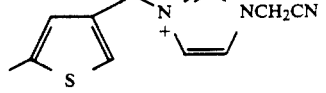 |
| 56 | H | —CH(OH)CH$_3$ | CN | |

TABLE I-continued

[Structure shown: carbapenem core with substituents R, R², R^a, and HAR-R₂^a on phenyl ring, with COO⁻ group]

| No. | R | R² | R^a | HAR-R₂^a |
|-----|---|----|----|----------|
| 57 | H | CH(OH)CH₃ | CN | [thiophene-CH₂-N⁺(imidazolium)-N-CH₂-CONH₂] |
| 58 | H | CH(OH)CH₃ | CN | [thiophene-CH₂-N⁺(imidazolium)-N-(CH₂)₃-OH] |
| 59 | H | CH(OH)CH₃ | CN | [thiophene-CH₂-N⁺(imidazolium)-N-CH₂CH₂-CONH₂] |
| 60 | H | CH(OH)CH₃ | CN | [thiophene-CH₂-N⁺(imidazolium)-N-(CH₂)₃-OH] |
| 61 | H | CH(OH)CH₃ | CN | [thiophene-CH₂-N⁺(imidazolium)-N-CH₂CH₂-CONH₂] |
| 62 | H | CH(OH)CH₃ | CN | [thiophene-CH₂-N⁺(imidazolium)-N-CH₂-CONH₂] |

The carbapenem compounds of the present invention are useful per se and in their pharmaceutically acceptable salt and ester forms in the treatment of bacterial infections in animal and human subjects. The term "pharmaceutically acceptable ester or salt" refers to those salt and ester forms of the compounds of the present invention which would be apparent to the pharmaceutical chemist, i.e., those which are non-toxic and which would favorably affect the pharmacokinetic properties of said compounds, their palatability, absorption, distribution, metabolism and excretion. Other factors, more practical in nature, which are also important in the selection, are cost of the raw materials, ease of crystallization, yield, stability, hygroscopicity, and flowability of the resulting bulk drug. Conveniently, pharmaceutical compositions may be prepared from the active ingredients in combination with pharmaceutically acceptable carriers. Thus, the present invention is also concerned with pharmaceutical compositions and methods of treating bacterial infections utilizing as an active ingredient the novel carbapenem compounds of the present invention.

The pharmaceutically acceptable salts referred to above may take the form —COOM. The M may be an alkali metal cation such as sodium or potassium. Other pharmaceutically acceptable cations for M may be calcium, magnesium, zinc, ammonium, or alkylammonium cations such as tetramethylammonium, tetrabutylammonium, choline, triethylhydroammonium, meglumine, triethanolhydroammonium, etc.

The pharmaceutically acceptable salts referred to above may also include non-toxic acid addition salts. Thus, the Formula I compounds can be used in the form of salts derived from inorganic or organic acids. Included among such salts are the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalene-sulfonate, nicotinate, oxalate, pamoate, pectinate, persulfate, 3-phenylpropionate, picrate, pivalate, propionate, succinate, tartrate, thiocyanate, tosylate, and undecanoate.

The pharmaceutical acceptable esters of the novel carbapenem compounds of the present invention are such as would be readily apparent to a medicinal chemist, and include, for example, those described in detail in U.S. Pat. No. 4,309,438, Column 9, line 61 to Column 12, line 51, which is incorporated herein by reference. Included within such pharmaceutically acceptable esters are those which are hydrolyzed under physiological conditions, such as pivaloyloxymethyl, acetoxymethyl, phthalidyl, indanyl and methoxymethyl, and those described in detail in U.S. Pat. No. 4,479,947, which is incorporated herein by reference.

The novel carbapenem compounds of the present invention may take the form COOM, where M is a readily removable carboxyl protecting group. Such conventional blocking groups consist of known ester groups which are used to protectively block the carboxyl group during the synthesis procedures described above. These conventional blocking groups are readily removable, i.e., they can be removed, if desired, by procedures which will not cause cleavage or other disruption of the remaining portions of the molecule. Such procedures include chemical and enzymatic hydrolysis, treatment with chemical reducing or oxidizing agents under mild conditions, treatment with a transition metal catalyst and a nucleophile, and catalytic hydrogenation. Broadly, such ester protecting groups include alkyl, substituted alkyl, benzyl, substituted benzyl, aryl, substituted aryl, allyl, substituted allyl and triorganosilyl. Examples of specific such ester protecting groups include benzhydryl, p-nitrobenzyl, 2-naphthylmethyl, allyl, 2-chloroallyl, benzyl, t-butyl, 2,2,2-trichloroethyl, t-butyldimethylsilyl, t-butyldiphenylsilyl, trimethylsilyl, 2-(trimethyl)silylethyl, phenacyl, p-methoxybenzyl, acetonyl, o-nitrobenzyl and 4-pyridylmethyl.

The compounds of the present invention are valuable antibacterial agents active against various Gram-positive and to a lesser extent Gram-negative bacteria and accordingly find utility in human and veterinary medicine. The antibacterials of the invention are not limited to utility as medicaments; they may be used in all manner of industry, for example: additives to animal feed, preservation of food, disinfectants, and in other industrial systems where control of bacterial growth is desired. For example, they may be employed in aqueous compositions in concentrations ranging from 0.1 to 100 parts of antibiotic per million parts of solution in order to destroy or inhibit the growth of harmful bacteria on medical and dental equipment and as bactericides in industrial applications, for example in waterbased paints and in the white water of paper mills to inhibit the growth of harmful bacteria.

The compounds of this invention may be used in any of a variety of pharmaceutical preparations. They may be employed in capsule, powder form, in liquid solution, or in suspension. They may be administered by a variety of means; those of principal interest include: topically or parenterally by injection (intravenously or intramuscularly).

Compositions for injection, a preferred route of delivery, may be prepared in unit dosage form in ampules, or in multidose containers. The compositions may take such forms as suspensions, solutions, or emulsions in oily or aqueous vehicles, and may contain formulatory agents. Alternatively, the active ingredient may be in powder form for reconstitution, at the time of delivery, with a suitable vehicle, such as sterile water. Topical applications may be formulated in hydrophobic or hydrophilic bases as ointments, creams, lotions, paints, or powders.

The dosage to be administered depends to a large extent upon the condition and size of the subject being treated as well as the route and frequency of administration, the parenteral route by injection being preferred for generalized infections. Such matters, however, are left to the routine discretion of the therapist according to principles of treatment well known in the anti-bacterial art. Another factor influencing the precise dosage regimen, apart from the nature of the infection and peculiar identity of the individual being treated, is the molecular weight of the chosen species of this invention.

The compositions for human delivery per unit dosage, whether liquid or solid, may contain from 0.1% to 99% of active material, the preferred range being from about 10-60%. The composition will generally contain from about 15 mg to about 1500 mg of the active ingredient; however, in general, it is preferable to employ a dosage amount in the range of from about 250 mg to 1000 mg. In parenteral administration, the unit dosage is usually the pure compound I in sterile water solution or in the form of a soluble powder intended for solution.

The preferred method of administration of the Formula I antibacterial compounds is parenteral by i.v. infusion, i.v. bolus, or i.m. injection.

For adults, 5-50 mg of Formula I antibacterial compounds per kg of body weight given 2, 3, or 4 times per day is preferred. Preferred dosage is 250 mg to 1000 mg of the Formula I antibacterial given two (b.i.d.) three (t.i.d.) or four (q.i.d.) times per day. More specifically, for mild infections a dose of 250 mg t.i.d. or q.i.d. is recommended. For moderate infections against highly susceptible gram positive organisms a dose of 500 mg t.i.d. or q.i.d. is recommended. For severe, life-threatening infections against organisms at the upper limits of sensitivity to the antibiotic, a dose of 1000 mg t.i.d. or q.i.d. is recommended.

For children, a dose of 5-25 mg/kg of body weight given 2, 3, or 4 times per day is preferred; a dose of 10 mg/kg t.i.d. or q.i.d. is usually recommended.

Antibacterial compounds of Formula I are of the broad class known as carbapenems or 1-carbadethiapenems. Naturally occurring carbapenems are susceptible to attack by a renal enzyme known as dehydropeptidase (DHP). This attack or degradation may reduce the efficacy of the carbapenem antibacterial agent. The compounds of the present invention, on the other hand, are significantly less subject to such attack, and therefore may not require the use of a DHP inhibitor. However, such use is optional and contemplated to be part of the present invention. Inhibitors of DHP and their use with carbapenem antibacterial agents are disclosed in the prior art [see European Patent Applications No. 79102616.4 filed Jul. 24, 1979 (Patent No. 0 007 614); and No. 82107174.3, filed Aug. 9, 1982 (Publication No. 0 072 014)].

The compounds of the present invention may, where DHP inhibition is desired or necessary, be combined or used with the appropriate DHP inhibitor as described in the aforesaid patents and published application. Thus, to the extent that the cited European patent applications 1.) define the procedure for determining DHP susceptibility of the present carbapenems and 2.) disclose suitable inhibitors, combination compositions and methods of treatment, they are incorporated herein by reference. A preferred weight ratio of Formula I compound: DHP inhibitor in the combination compositions is about 1:1. A preferred DHP inhibitor is 7-(L-2-amino-2-carboxyethylthio)-2-(2,2-dimethylcyclopropanecarboxamide)-2-heptenoic acid or a useful salt thereof.

The invention is further defined by reference to the following examples, which are intended to be illustrative and not limiting.

All temperatures are in degrees Celsius.

STARTING MATERIAL SYNTHESIS

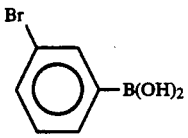

3-BROMOPHENYLBORONIC ACID

N-Butyllithium (2.5M; 44 mL; 0.11M) was added dropwise over 15 mins. to a vigorously stirred solution of m-dibromobenzene (25 g; 0.106M) in 500 mL of anhydrous ether at −78° under nitrogen. After stirring 10 mins. more, a solution of triisopropylborate (25.3 mL; 0.11M) in anhydrous ether (200 mL) was added over 20 mins. The cooling bath was then removed, and the stirring solution was allowed to warm to R.T. over ~2 hrs. A small amount of solid separated. After stirring 15 mins. more at R.T., 150 mL of ice cold 8% aqueous hydrochloric acid was cautiously added, and the stirring was continued for 15 mins. The organic phase was separated, washed with 2×100 mL of saturated sodium chloride solution, and dried over anhydrous magnesium sulfate. Solvent removal gave ~30 G of crude product as a semi-solid, which was shaken well with 150 mL of hexane. The solid was filtered and washed with 2×25 mL of hexane. The resulting silky solid (mp 178°-9° C. after softening at ~160° C.) (6.5 g) was used as 3-bromophenylboronic acid with a small amount of contamination. The hexane filtrate was concentrated and the residue was stirred well with 150 mL of petroleum ether (30°-60°). The resulting solid was filtered and washed with 2×25 mL of petroleum ether. This resulting solid (4.4 g) melting at 178.3°-179° C. was the desired 3-bromophenylboronic acid. NMR: 7.38-7.46; 7.70-7.80; 8.1-8.18; 8.31 (aromatic H's)

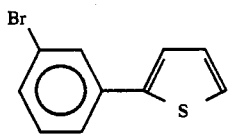

2-(3'-BROMOPHENYL)THIOPHENE

To a stirred solution of m-bromoaniline (34.4 g; 0.2M) in thiophene (200 mL) was added isoamylnitrite (46.86 g; 0.4M) dropwise over a period of 30 mins. at 0° C. The resulting mixture was cautiously warmed to R.T. and heated to reflux for 16 hours. The reaction mixture was cooled, diluted with 400 mL of ether, washed with 3×100 mL of satd. sodium chloride solution, and dried over anhydrous magnesium sulfate. Solvent and excess thiophene were removed. A solution of the residue in 200 mL of ether was filtered through 50 G silica gel bed. Solvent was removed, and the residue was distilled to give 34% of 2-(3'-bromophenyl) thiophene as a yellow liquid boiling at 130°-2°/~0.2 mm. This liquid solidified on standing in the refrigerator.
NMR: 7.06-7.78

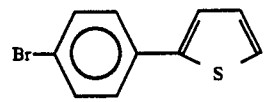

2-(4'-BROMOPHENYL)THIOPENE

Similarly, 2-(4'bromophenyl)thiophene was prepared from 4-bromo aniline in 29% yield as a yellow oil boiling at 146°-8°/~0.5 mm.

NMR: (C$_6$D$_6$): 6.68-6.92(thiophene H's) 7.03-7.20 (p-phenyl H's).

2-PHENYLTHIOPHENE

The above method was used to prepare 2-phenylthiophene from aniline in 11% yield as colorless liquid boiling at 110°-113°/~3 mm.

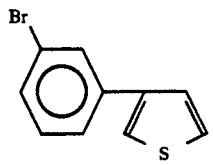

3-(3'-BROMOPHENYL)THIOPHENE

The thiophene was prepared according to G. Martelli et al., J. Chem. Soc (B)., 901, (1968).

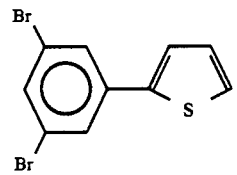

2-(3',5'-DIBROMOPHENYL)THIOPHENE 3,5-dibromoaniline was treated as described in the procedure for 2-(3'-bromophenyl)thiophene to give 2-(3',5'-dibromophenyl)thiophene in 55% yield as a yellow oil, which solidified as a glassy solid.

NMR: 7.04-7.68 (aromatic H's)

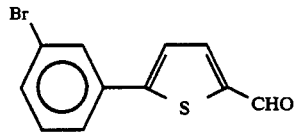

2-FORMYL-5-(3'-BROMOPHENYL)THIOPHENE

Phosphorus oxychloride (1.15 mL; 15.4 mM) was added slowly to stirring dimethylformamide (0.95 mL; 12.2 mM) at −10° under nitrogen. The resulting mixture was stirred for 15 mins. 2-(3'-bromophenyl)thiophene (2.12 g; 9 mM) was then added. The reaction mixture was then warmed slowly to 110° over a period of 1 hr. cooled and poured into ice, and cautiously neutralized with sodium carbonate. Extraction with ethyl acetate and drying the organic phase with anhydrous magnesium sulfate provided upon concentration 2.16 g of the desired aldehyde as an oily solid.

NMR: 7.26–7.84 (aromatic H's); 9.92(—C(O)H; S)

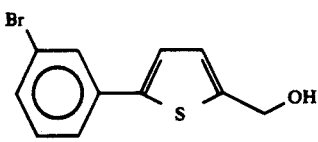

2-(HYDROXYMETHYL)-5-(3'-BROMOPHENYL)-THIOPHENE

Sodium borohydride (400 mg; 10 mM) was added portionwise over 5 min. to a stirred suspension of the above crude aldehyde (2.16 g) in 100 mL of methanol at 0° C. The resulting clear solution was stirred 30 mins. Solvent was then removed in vacuo at R.T. The residue was taken up in 50 mL of ethyl acetate, washed with 3×20 mL of sat'd. sodium chloride solution, and dried over anhyd. magnesium sulfate. Solvent removal followed by silica gel chromatography with methylene chloride gave 1.355 g of desired alcohol as an amorphous solid.

NMR: 1.83 (OH; t; J-6H3); 4.82(CH$_2$; d; J-6H$_3$); 6.96–7.75 (aromatic H's)

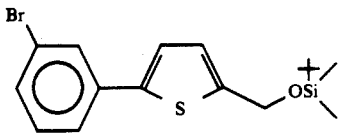

2-(t-BUTYLDIMETHYLSILYLOXYMETHYL)-5-(3'-BROMOPHENYL)THIOPHENE

To a stirred solution of 2-(hydroxymethyl)-5-(3'-bromophenyl)thiophene (1.08 G; 4 mM) and triethylamine (1.4 mL; 10 mM) in 20 ml of methylene chloride at R.T. was added t-butyldimethylchlorosilane (1.5 g; 10 mM). This mixture was stirred overnight, diluted with 30 ml of ethyl acetate, washed with 2×15 ml of sat'd. sodium chloride solution, and dried over anhyd. magnesium sulfate. Solvent was removed to give a residue, which was purified on silica gel with ether:petroleum ether (1:20) as solvent mixture. Eluate was distilled to give 0.99 g of 2-(t-butyldimethylsilyloxymethyl)-5-(3'bromophenyl)thiophene as colorless liquid boiling at 167°–170°/~0.2 mm.

NMR: 0.17 and 0.95 (silyl methyls); 4.88 (s, CH$_2$); 6.88–7.75 (aromatic H's)

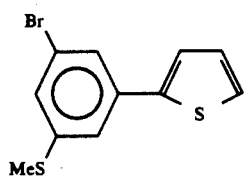

2-[3'-BROMO-5'-METHYLTHIO)PHENYL]THIOPHENE 2.5M n-Butyllithium (1.5 mL; 3.75 mM) was added dropwise to a solution of 2-(3',5'-dibromophenyl)thiophene (1.06 g; 3.33 mM) in anhydrous tetrahydrofuran (7 mL) at −78° under nitrogen. The reaction mixture was then stirred 10 min. and a solution of dimethyldisulfide(0.9 mL; 10 mM) in 3 mL of anhydrous tetrahydrofuran was added. The resulting mixture was stirred overnight at R.T. after which 5 mL of sat'd. ammonium chloride and 20 mL of ethyl acetate were added. The organic phase was separated, washed with 2×10 mL of sat'd. sodium chloride solution, and dried over anhyd. magnesium sulfate. Solvent removal, and purification on silica gel using hexane as solvent gave a liquid, which was distilled to give 52% of 2-[(3'-bromo)-(5'-methylthio)]phenylthiophene as a colorless oil boiling at ~150°–152°/~0.2 mm. (oil bath temp. 180°)

NMR: 1.52(SCH$_3$; s); 7.00–7.50 (aromatic H's)

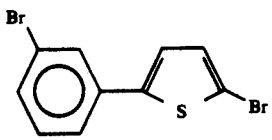

2-BROMO-5-[3'-BROMOPHENYL]THIOPHENE

A solution of bromine (8 g; 50 mM) in 20 mL of glacial acetic acid was added dropwise to a vigorously stirred solution of 2-(3'-bromophenyl)thiophene (12 g; 50 mM) in 80 mL of glacial acetic acid. The resulting mixture was heated to reflux 5 hrs, cooled and poured onto ice. A solid separated which was filtered and washed with ice water, and purified on silica gel using hexane as solvent to give 68% of 2-bromo-5-[3'-bromophenyl]thiophene as an amorphous solid.

NMR: 7.00–7.68 (aromatic H's)

3-(3'-BROMOPHENYL)-5-BROMOTHIOPHENE

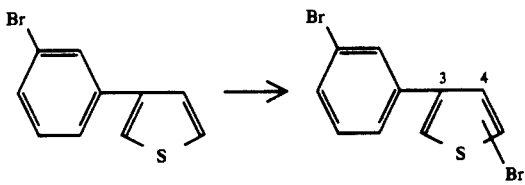

To a solution of 3-(3'-bromophenyl)thiophene, (G. Martelli et al., J. Chem. Soc., (B), 901, 1968) (712 mg, 3 mmol) in acetic acid (6.2 ml) with stirring under N$_2$, a solution of Br$_2$ (154 μl, 3 mmol) in acetic acid (4.8 ml) was added dropwise. The resultant orange-red solution was heated for 5 hours at 100° C. After cooling, the reaction mixture was poured into ice water with stirring. A non-filterable milky precipitate was extracted 2× with Et$_2$O. The combined Et$_2$O layers were carefully extracted 3× with NaHCO$_3$ solution and then 2× with brine. After drying (MgSO$_4$), filtering and concentrating, the residue was chromatographed on a column of Bakers Si Gel (60–200 mesh) packed, applied and eluted with hexane. Those fractions containing the slightly less polar product were combined and concentrated in vacuo (763 mg). Preparative TLC of 663 mg of this material on 7–1000 μSi Gel GF plates (eluting with hexane and extracting with CH$_2$Cl$_2$) provided a purer sample of the desired 5-bromo isomer (416 mg) (i.e., less of the undesired 2-bromo isomer was present). Approximately 162 mg of this material was further purified by preparative TLC on 4–1000μ Si Gel GF (eluting and extracting as above) to give 3-(3'-bromophenyl)-5-bromothiophene pure enough for further reaction (196 mg).

MS: m/z 316/318/320 (MI).

¹H NMR (300 MHz, CDCl₃)): δ7.01 (d, J=6 Hz, H₄ of 2-Br compound); 7.23-7.70 (series of m's, phenyl and thiophene protons of the minor 2-Br and the desired 5-Br isomers).

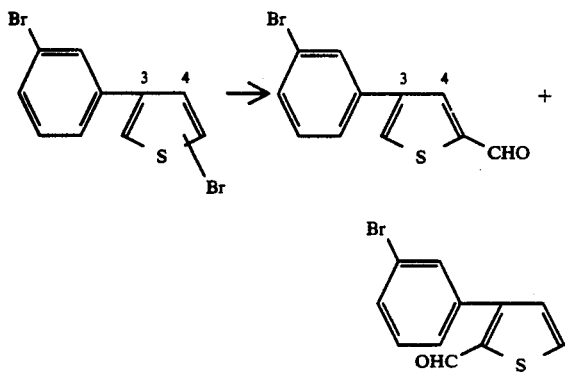

3-(3'-BROMOPHENYL)-5-THIOPHENE CARBOXALDEHYDE

To a solution of the brominated thiophene (mainly the correct 5-bromo isomer; 196 mg, 0.62 mmol) in ether (2.7 ml) at −78° C. under N₂, 1.6M BuLi in hexane (388 µl, 0.62 mmol) was added dropwise. After 15 min. at −78°, DMF (63 µl, 0.81 mmol) was added, and the reaction mixture was stirred overnight at ambient temperature. The reaction was partitioned between EA and brine. After phase separation, the organic layer was again extracted with brine, dried, filtered and concentrated to provide crude formylated product (151 mg). Preparative TLC on 3-1000µ Si Gel GF plates (eluting with 20% Et₂O/hexane and extracting with CH₂Cl₂) provided a major band containing a mixture (80 mg) of the desired 5-formyl isomer contaminated with a small amount of the 2-formyl isomer.

MS: m/z 266/268 (MI.)
IR(CH₂Cl₂): 1670 (formyl) cm⁻¹
¹H NMR (300 MHz, CDCl₃): δ7.22 (low amplitude d, J=5 Hz, H₄ of minor amount of 2-formyl); 7.29-8.00 (series of m's phenyl and thiophene protons); 9.88 (d, J=1 Hz, long range splitting minor amount of 2-formyl); 9.98 (d, J=1 Hz, CHO of 5-formyl, allylic splitting).

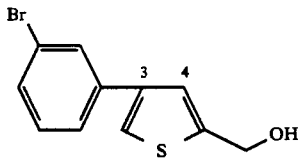

3-[(3'-BROMOPHENYL)-(5-HYDROXYMETHYL)]THIOPHENE

To a solution of the formylated thiophene (79 mg, 0.3 mmol) stirred in MeOH (3 ml) at 0°, NaBH₄ (13.6 mg, 0.34 mmol) was added, and stirring was continued for 40 min. Upon concentration to an oil under a N₂ stream, the residue was partitioned between EA and brine, the organic layer was again washed with brine, dried, filtered and concentrated in vacuo to give the crude product (77 mg). Preparative TLC on 2-1000µ Si Gel GF plates (eluting with CH₂Cl₂ and extracting the major UV band with 10% MeOH/CH₂Cl₂) provided the purified 5-hydroxymethyl compound (70 mg, 88% yield). A small amount of faster running material (5 mg, 6% yield) proved to be the undesired 2-hydroxymethylthiophene compound having the widely split H4-doublet (J=4.5 Hz). The desired product contained none of this impurity.

MS: m/z 268/250(MI)
IR(CHCl₂): 3600(OH) cm⁻¹
¹H NMR (300 MHz, CDCl₃): δ1.84 (t, J=6 Hz, OH); 4.85(dd, J=0.5 (allylic coupling to H₄) and 6 Hz; CH₂OH); 7.24, 7.42, 7.50 and 7.70 (4 sets of m's; phenyl and thiophene H's).

NMR data for the less polar 2-hydroxymethylthiophene (5 mg above):
¹H NMR (300 MHz, CDCl₃): δ1.81 (t, J=6 Hz, OH); 4.82 (d, J=6 Hz, CH₂OH); 4.86 (br d, J=6 Hz, CH₂OH of small amount of 5-isomer); 7.08 (d, J=5 Hz, H₄): 7.25-7.71 (series of multiplets, phenyl and thiophene protons).

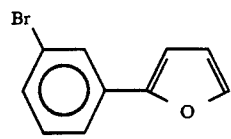

3-(3'-BROMOPHENYL)-5-(t-BUTYLDIMETHYL-SILYLOXYMETHYL)THIOPHENE

To a solution of the 5-hydroxymethyl thiophene (62 mg, 0.23 mmol) in CH₂Cl₂ (1.1 ml) at 0° C. with stirring under N₂, TBDMSiCl (183 mg, 0.55 mmol) and Et₃N (80 µl, 0.59 mmol) were added. The cooling bath was removed, and the reaction mixture was stirred overnight at ambient temperature. Work-up of an aliquot showed incomplete conversion. Therefore, DMF (20 µl) in CH₂Cl₂ (1 ml) was added, and stirring was resumed for a few hours*. Brine containing 1M K₂HPO₄ (1 ml) and additional CH₂Cl₂ were added to the reaction mixture with stirring. After phase separation, the aqueous layer was again extracted with CH₂Cl₂, and the combined organic layers were washed with brine, dried, filtered and concentrated in vacuo to give the crude product (97 mg). Preparative TLC on 2-1000µ Si Gel GF plates (eluting with 20% Et₂O/hexane and extracting with CH₂Cl₂) provided the purified 5-silyloxymethyl thiophene (79 mg, 90% yield).

*In later runs, the DMF was introduced initially [i.e., starting material (820 mg); CH₂Cl₂ (10.5 ml); TBDMSiCl (820 mg); Et₃N (788 µl); DMF (830 µl)] and overnight reaction provided complete silylation.

MS: m/z 325/327 (MI - t-butyl); 251/253 (MI - OTBDMSi).

¹H NMR (300 MHz, CDCl₃): δ0.13 (s, Si(CH₃)₂); 0.94 (s, t-butyl-Si); 4.89 (s, CH₂OTBDMSi); 7.16-7.70 (series of m's, phenyl and thienyl H's).

2-(3'-BROMOPHENYL)FURAN

BP: 98°–105°/0.1 mm

Reference: E. L. Plummer, J. Agric. Food Chem., 31, 718–721 (1983).

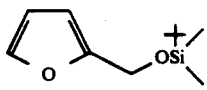

2-(t-BUTYLDIMETHYLSILYLOXYMETHYL)FURAN

To a stirring mixture of 2-furan methanol (33 g, ~0.335M) and triethylamine (47 mL, ~0.335M) in anhydrous methylene chloride (200 mL) under nitrogen was added t-butyldimethylchlorosilane portionwise at room temperature. 20 mL of N,N-dimethylformamide was added. The resulting mixture was stirred 3 hrs. After dilution with 400 mL of ether, the reaction mixture was washed with 3×100 mL of ice-water, 100 mL of saturated sodium chloride solution, and dried over anhydrous magnesium sulfate. Solvent removal gave a crude product, which was distilled to afford 39.8 g of the desired silyl ether as a colorless liquid boiling at 76°-7°/~0.5 mm.

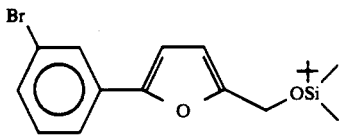

2-(3'-BROMOPHENYL)-5-(t-BUTYLDIMETHYLSILYLOXYMETHYL)FURAN

To a stirred solution of m-bromoaniline (6.88 g; 0.04M) in 42.2 g (0.2M) of 2-(t-butyldimethylsilyloxymethyl)furan at 0° was added isoamylnitrite (10.75 mL; 0.08M) dropwise over a period of 0.5 hr. The resulting mixture was then heated 16 hours at 50° C. The reaction mixture was cooled and diluted with 150 mL of ether and washed with 2×100 mL of ice cold water. The organic phase was dried over anhydrous magnesium sulfate, and the residue was distilled after filtering through 50 G of silica gel bed, to give 26% of the desired 2-(3'-bromophenyl)-5-(t-butyldimethylsilyloxymethyl)furan as a colorless liquid boiling at 163°-7°/~0.5 mm.

STEP A1: GENERAL SYNTHESIS OF ARYLKETONES

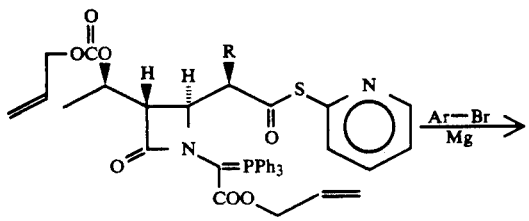

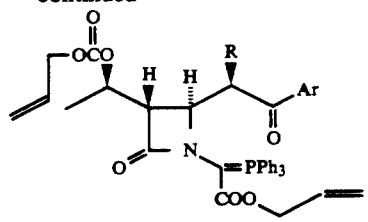

METHOD 1

Aryl bromide (1 mM) was added to a stirred suspension of magnesium chips (1.25 mM) in 2 mL of anhydrous tetrahydrofuran under nitrogen at R.T. 8 μL of 1,2-dibromoethane was then added. The resulting mixture was stirred 3 hours, when most of the metal was digested. The resulting dark yellow solution was used as 0.5M solution of the aryl Grignard reagent.

This Grignard reagent solution was added dropwise to a stirred solution of (3S, 4R)-1-[[(allyloxy)carbonyl](-triphenylphosphoranylidene)methyl]-3-[(1R)-1-[(allyloxy)carbonyloxy]ethyl]-4-[[2'-pyridylthio)carbonyl]-methyl]azetidin-2-one, (~0.5 mM) in 2 mL of anhydrous tetrahydrofuran at 0° under nitrogen. The reaction mixture was stirred 15 mins at 0°. Satd ammonium chloride solution (5 mL) and 10 mL of ethyl acetate were added. The organic layer was separated, and washed with 2×5 mL of satd sodium chloride solution and dried over anhyd magnesium sulfate. Solvent removal followed by silica gel chromatography using mixtures (1:1 to 2:1) of ethyl acetate:hexane as eluent gave the desired ylid arylketone as a pale yellow foam.

METHOD 2

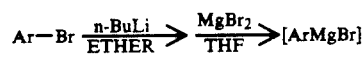

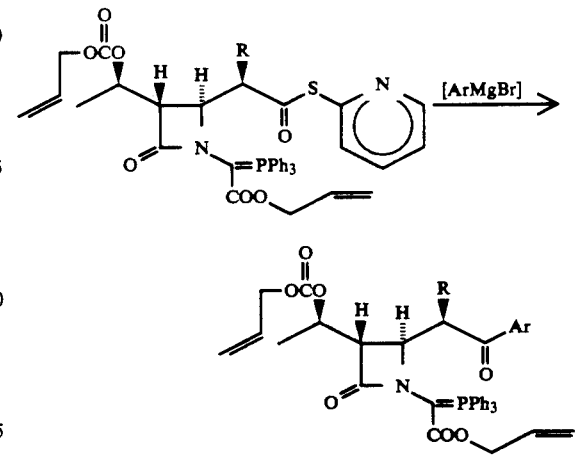

To a stirred solution of 3 mM aryl bromide in anhydrous ether (12 mL) at −78° under nitrogen was added n-butyllithium (2.5 molar solution; 1.32 mL; 3.3 mM) dropwise. The resulting mixture was stirred 0.5 hr. A solution of magnesium bromide, freshly prepared by stirring 6.6 mM of magnesium turnings in 24 mL of anhydrous tetrahydrofuran with 6 mM of 1,2-dibromoethane for about 1 hr under nitrogen at ambient temperature, was then added dropwise to the above stirring lithium salt at −78°. The resulting mixture was stirred 15 mins at −78°, and 30 mins at 0°. The thus obtained turbid solution was used as a 0.0833 molar solution of the required aryl magnesium bromide.

This solution of the Grignard reagent was added slowly to a stirred solution of 1.4 mM of (3S, 4R)-1-[[allyloxy)carbonyl](triphenylphosphoranylidene)methyl]-3-[(1R)-1-[(allyloxy)carbonyloxy]ethyl]-2-[[(2'-pyridylthio)carbonyl]methyl]azetidin-2-one, in 5 mL of anhydrous tetrahydrofuran at 0° under nitrogen. The reaction mixture was stirred 15 mins. at 0°, and satd. ammonium chloride (15 mL) and 30 mL of ethyl acetate were added. The organic layer was separated, washed with 2×15 mL of sat'd. sodium chloride solution, and dried over anhydrous magnesium sulfate. Solvent removal and purification on silica gel using a (1:1 to 2:1) mixture of ethyl acetate:hexane gave the desired aryl ketone, as a light yellow foam.

STEP A2: DESILYLATION OF THE YLIDE SILYLETHER KETONE TO YLIDE ALCOHOL KETONE

A solution of the arylketone (from Step A1) (220 mg) was dissolved in 3.5 mL of an ice-cold mixture of 2% $H_2SO_4$ in methanol. After stirring the mixture 75 mins at 0°, it was diluted with 5 mL of ethyl acetate and washed with 3×5 mL of 10% sodium bicarbonate solution followed by 5 mL of saturated sodium chloride solution and dried over anhyd. magnesium sulfate. Solvent removal afforded 163 mg of almost pure alcohol as white foam.

STEP B1: GENERAL PROCEDURE FOR CYCLIZATION

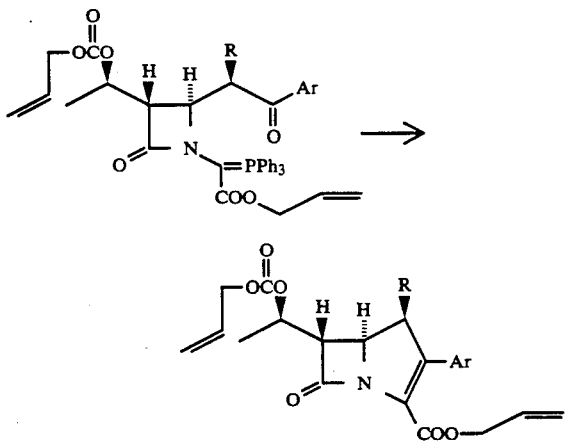

A solution of the ylid ketone (0.25 mM) in 2 mL of p-xylene containing a tiny crystal of hydroquinone was heated 45 mins. to 3 hours (depending on the nature of R) at 130° C. under nitrogen. The solution was cooled, applied in a suitable solvent to a silica gel column packed with hexane and then eluted first with hexane and then with 4:1 to 2:3 mixtures of hexane:ethyl acetate to give the desired carbapenem analogs.

STEP B2: GENERAL PROCEDURE FOR QUATERNIZATION

To a solution of 120 mg (0.2 mm) of the carbapenem carbinol from Step B2 in 3 mL of methylene chloride at 0° under nitrogen were added 0.5 mm of amine, and 0.25 mm of trifluoromethane sulfonic anhydride. After stirring 15 mins at 0°, the reaction mixture was diluted with 10 mL of methylene chloride and washed with 5 mL of ice water. The organic phase was dried over anhydrous magnesium sulfate. Solvent removal afforded 118 mg of the desired quaternary salt as yellow foam.

STEP C: GENERAL PROCEDURE FOR DEALLYLATION

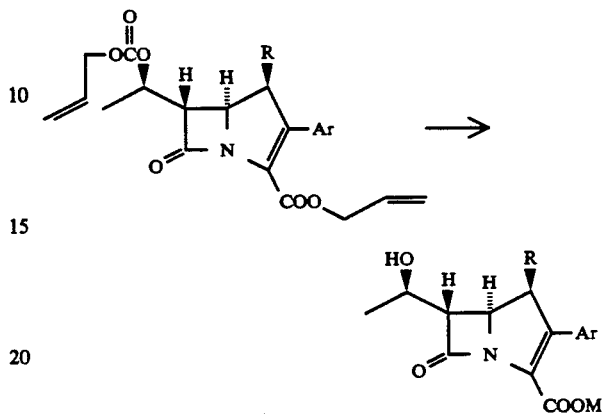

To a stirred solution of the carbapenem (0.2 mM) in 3 mL of a 1:1 mixture of methylene chloride: ether in a centrifuge tube at 0° under nitrogen were added 2-ethylhexanoic acid (0.2 mM), triphenylphosphine (0.05 mM), tetrakis-(triphenylphosphine)palladium (0.04 mM), and 0.2 mM of sodium or potassium 2-ethylhexanoate. This mixture was stirred 2 hrs when a solid precipitated out. After diluting with 10 mL of ether, the mixture was centrifuged and the supernatant liquid was decanted. The remaining solid was stirred with 2 mL of ethyl acetate and centrifuged. The resulting solid was dissolved in 1 mL of water and applied to a 1000 µ reverse phase silica gel plate. Elution with mixtures of acetonitrile:water or EtOH:water gave an ultraviolet active area, which was scraped and stirred with 5 mL of 4:1 acetonitrile:water mixture. The solid was filtered and washed with 3×2 mL of a 4:1 acetonitrile:water mixture. The filtrate was washed with 4×10 mL of hexane, concentrated to 1 mL in vacuo at R.T. and lyophilized to give the sodium or potassium salt of the carbapenem as a white to creamy, fluffy mass.

In the following examples:
the IR data are in $cm^{-1}$;
the UV data are in nanometers for $\lambda_{max}$ water; and
the NMR spectra are measured in $CDCl_3$ solvent unless otherwise specified.

EXAMPLE 1

STEP A
STEP A1: PREPARATION OF YLIDE KETONE
STEP A2: DESILYLATION OF SILYL ETHER
STEP A1:

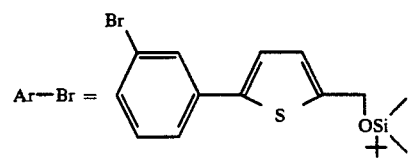

Conditions:
1) Mg/THF; 3 hr./R.T.
2) 0°; 15 min; THF; pyridylthioester

Yield: 67%
STEP A2
Conditions: CH₃OH/H₂SO₄; 0°; 1.25 hrs
Yield: 81%
STEP B
STEP B1: CYCLIZATION OF YLIDE KETONE TO CARBAPENEM
STEP B2: QUATERNIZATION OF CARBINOL
Conditions
B1: Xylene; 130°; 1.5 hrs.
Yield: 83%

B2:

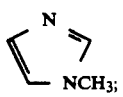

triflic anhydride; CH₂Cl₂; 0°; 15 min.
Spectra:
IR: 1775; 1745; 1720
NMR: H6: 3.42–3.50; dd; J=3 and 8 Hz H5: 4.24–4.36; ddd; J=3, 9 and 10 Hz NCH₃: 3.96 (s); N⁺CH₂: 5.62 (s); N⁺=CHN: 9.44 (s)
STEP C: DEALLYLATION
Conditions: PPh₃; Pd(PPh₃)₄

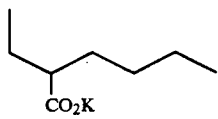

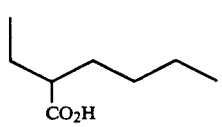

CH₂Cl₂; 0°; 4 hrs
Yield: 67%
Spectra:
UV: 292
ε ext 5074

EXAMPLE 3

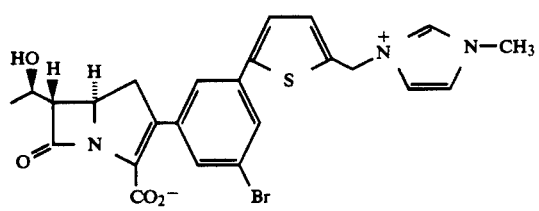

STARTING MATERIAL SYNTHESIS

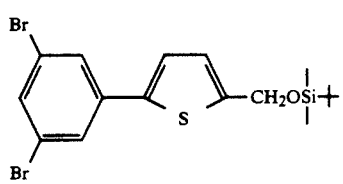

2-(t-BUTYLDIMETHYLSILYLOXYMETHYL)-5-(3',5'-DIBROMOPHENYL)THIOPHENE
FORMYLATION
Conditions:
1) POCl₃, DMF; 0°; 10 min
2) 2-(3',5'-dibromophenyl)thiophene; 110°–120°; 1.5 hours
Yield: 40%
Spectra:
IR: 1670(CHO) cm⁻¹.
¹H NMR (300 MHz, CDCl₃); δ7.4–7.76 (phenyl and thiophene H's); 9.92 (CHO).
REDUCTION
Conditions:
1) NaBH₄/MeOH
2) 0°; 1 hour
Yield: 99%
Spectra:
MS m/z: 346, 348, 350 (MI).
¹H NMR (300 MHz, CDCl₃): δ1.82 (t, OH); 4.84 (d, CH₂OH); 6.88 and 7.18 (thiophene protons); 7.55–7.64 (phenyl protons)
SILYLATION
Conditions:
1) TBDMSiCl; Et₃N; DMF/CH₂Cl₂
2) R.T.; few hours; 10°; o.n.
Yield: 95%
Spectra:
MS m/z: 460, 462, 464 (MI); 403, 405, 407 (MI-t-butyl)
¹H NMR (300 MHz, CDCl₃); δ0.12 (s, Si(CH₃)₂); 0.94 (s, t-butyl); 4.86 (s, CH₂O); 6.87–7.62 (phenyl and thiophene protons)

CARBINOL PREPARATION

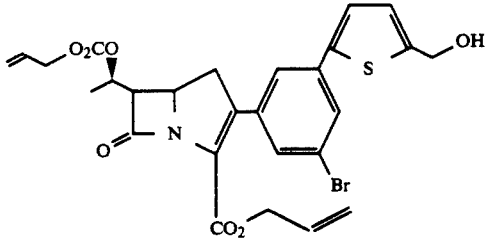

STEP A1: PREPARATION OF YLIDE KETONE
STEP A2: DESILYLATION OF SILYL ETHER TO CARBINOL

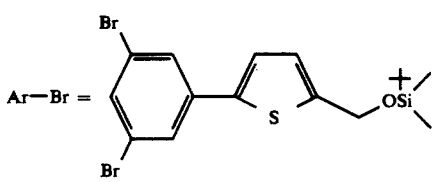

Conditions:
A1:
1) Mg/THF; 3 hrs.; R.T.
2) 0°; 15 min; pyridylthioester
Yield: 23% of ylide ketone
Spectra;
IR: 1740; 1690; 1645; 1620
A2: CH₃OH; H₂SO₄

Yield: 72% of carbinol
Spectra:
IR: 3100(OH); 1740; 1685; 1620
STEP B
Conditions: Xylene; 130°; 3 hrs.
Yield 81%
Spectra:
IR: 3500(OH); 1740; 1720
NMR: OH: 1.96–2.06; t; J=6 Hz CH$_2$O: 4.80–4.86; d; J=6 Hz H6: 3.40–3.49; dd; J=3 and 8 Hz H5: 4.24–4.38; ddd; J=3, 8.5 and 9.5 Hz

QUATERNIZATION OF CARBINOL

Conditions:
1) 2.5 eq. 1-methylimidazole/CH$_2$Cl$_2$
2) 1.1 eq triflic anhydride
3) 0°; 45 min.
Yield: 85%
Spectra:
$^1$H NMR (300 MHz, CDCl$_3$): δ1.48 (d, CH$_3$); 3.49 (dd, H6); 3.96 (s, N—CH$_3$); 5.58 (thiophene-CH$_2$—); 9.26 (s, N=CH—N).

DEALLYLATION

Conditions: PPH$_3$; Pd(Ph$_3$)$_4$

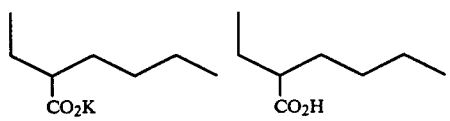

CH$_2$Cl$_2$/EtOAc; 2 hours
Yield: 31%
Spectra:
UV(H$_2$O): λmax=295 mµ
$^1$H NMR (300 MHz, D$_2$O): (no internal standard—DOH at 4.80); δ1.24 (d, CH$_3$CHOH—); 3.37 (dd, H6); 3.80 (s, N—CH$_3$); 5.50 (s, thiophene-CH$_2$—); 8.78 (s, N=CH—N).

EXAMPLE 4

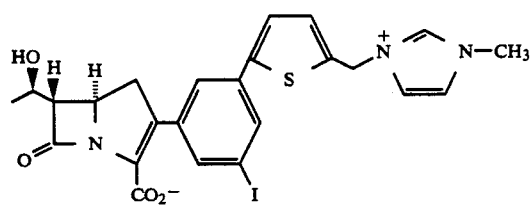

STARTING MATERIAL SYNTHESIS

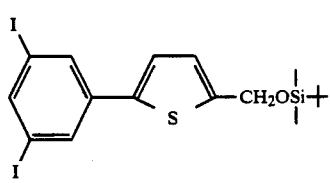

2-(t-BUTYLDIMETHYLSILYLOXYMETHYL)-5-(3',5'-DIIODOPHENYL)THIOPHENE

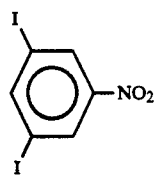

3,5-DIIODONITROBENZENE 13.8 g (0.2M) of sodium nitrite was added portionwise slowly to 96 mL of conc. sulfuric acid at 0° C. The resulting thick mixture was stirred at 0° C. for 10 minutes. A suspension of 68.25 g (0.175M) of finely powdered 4-nitro-2,6-diiodoaniline in 175 mL of glacial acetic acid was added cautiously portionwise to the above mixture at 0° C. After the addition, the mixture was stirred 30 mins. The resulting slurry was then added slowly to a vigorously stirred suspension of 4 g of cuprous oxide in 420 mL of absolute ethanol over a period of 25 mins. Vigorous effervescence was observed during this addition. The resulting mixture was stirred 20 mins. at room temperature and then heated to reflux for 30 minutes. After cooling, this reaction mixture was poured onto a large amount of ice. The solid which separated was filtered, and washed with water. This solid was dissolved in a minimum amount of chloroform, dried over anhyd. magnesium sulfate, and the solvent was removed to give 62 g of 3,5-diiodnitrobenzene as a yellow solid.

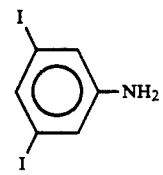

3,5-DIIODOANILINE

A mixture of 61.5 g (0.164M) of 3,5-diiodonitrobenzene and 111.1 g (0.4924M) of stannous chloride in 900 mL of ethanol was heated to reflux 1.5 hrs under nitrogen. The reaction mixture was cooled and most of the solvent was removed in vacuo. The residue was partitioned between ethyl acetate and excess ice-cold 5N sodium hydroxide and ice. The organic phase was separated, washed with sat'd sodium chloride solution, and dried over anhyd. magnesium sulfate. Solvent removal afforded a crude oil which was purified on silica gel using 8:1:1 mixture of hexane:methylene chloride:ethyl acetate to give 35 g of 3,5-diiodoaniline as a light tan colored solid.

DIAZOTIZATION AND CONDENSATION

Conditions:
1) Diiodoaniline;thiophene as solvent and reactant
2) isoamylnitrite
3) 60°; 2 hours
Yield: 23%
Spectra:
MS m/z: 411.71 (MI)

¹H NMR (400 MHz, CDCl₃): δ7.06–7.35 (m's; thiophene protons); 7.88–7.94 (m's, phenyl protons).

FORMYLATION

Conditions:
1) POCl₃; DMF; 0°; 10 min
2) 2-(3',5'-diiodophenyl)thiophene from above; 110°; 3 hours Yield: 77% (used immediately)

REDUCTION

Conditions:
1) NaBH₄/MeOH
2) 0°; 1.5 hours

Yield: 69%

Spectra:
¹H NMR (400 MHz, CDCl₃): δ1.79 (t, OH); 4.8 (d, CH₂OH); 6.95 and 7.13 (2d's, thiophene protons); 7.80–7.94 (phenyl protons)

SILYLATION

Condition:
1) TBDMSiCl; Et₃N; DMF/CH₂Cl₂
2) R.T.; few hours; 10°; o.n.

Yield: 97%

Spectra:
¹H NMR (400 MHz, CDCl₃): δ0.12 (s, 0.12); 0.94 (s, t-butyl); 4.84 (s, CH₂OSi); 6.87 and 7.12 (2d's, thiophene protons); 7.85–7.91 (phenyl protons).

PREPARATION OF YLIDE KETONE

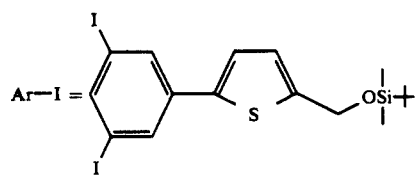

Conditions:
1) t-BuLi/THF; −78° to −20° (5 min)
2) MgBr₂/THF; −20°; 5 min
3) Pyridylthioester; 0°; 4 hours Yield: 25%

Spectra:
MS m/z: 1028 (M+1); 262 (Ph₃P).

¹H NMR (400 MHz, CDCl₃): δ0.15 (s, Si(CH₃)₂); 0.95 (s, t-butyl); 1.18 (d, CH₃); 4.86 (CH₂O); 5.8–5.98 (m, CH₂=CH—CH₂—).

DESILYATION OF KETONE YLIDE TO CARBINOL

Conditions:
1) aq. HCl/MeOH
2) 0°; 1.25 hours

Yields: 90%

Spectra:
MS m/z: 914 (M+1); 262 (PH₃P).

¹H NMR (400 MHz, CDCl₃): δ1.16 (d, CH₃); 4.78 (dd, H6); 5.8–6.0 (m, CH₂=CH—CH₂—)

CYCLIZATION OF CARBINOL YLIDE TO CARBAPENEM

Conditions: Benzene; 80°; o.n.
Yield: 89%

Spectra:
MS m/z: 636 (MI+1); 618 (MI-OH)

IR: 1787 (β-lactam C=O); 1750 and 1725 (C=O's) cm⁻¹

¹H NMR (400 MHz, CDCl₃); δ1.50 (d, CH₃); 1.81 (t, OH); 3.44 (dd, H6); 4.31 (m, H5); 6.98 and 7.16 (2d's, thiophene protons); 7.50–7.87 (phenyl protons).

QUATERNIZATION OF CARBINOL

Conditions:
1) 2.4 eq. 1-methylimidazole/CH₂Cl₂
2) 1.2 eq. triflic anhydride
3) 0°; 45 min Yield: 84% (used immediately)

DEALLYLATION

Conditions: PPh₃; Pd(PPh₃)₄

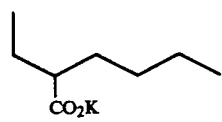

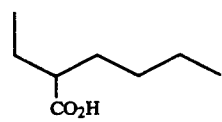

1:1 CH₂Cl₂:EtOAc; 2 hours
Yield: 9%

Spectra:
UV (H₂O): λmax=296 mμ

¹H NMR (400 MHz, 2:1 D₂O: CD₃CN) (no internal standard —DOH at 4.80); δ1.47 (d, CH₃CHOH—); 3.63 (dd, H6); 4.05 (s, N-CH₃); 5.75 (s, thiophene CH₂N—); 7.45–8.05 (thiophene, N—CH=CH—N, and phenyl protons); 8.98 (partially exchanged N=CH—N).

EXAMPLES 5, 6, and 7

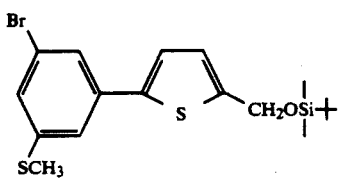

where: n = 0, 1, 2

STARTING MATERIAL SYNTHESIS 2-(t-BUTYLDIMETHYLSILYLOXYMETHYL)-5-(3'-BROMO-5'-METHYLTHIOPHENYL)THIOPHENE

Conditions:

1) 2-(t-butyldimethylsilyloxymethyl)-5-(3',5'-dibromophenyl)thiophene; 1.1 eq. BuLi/THF; −78°; 5 min
2) excess (CH₃S)₂; −78° to r.t. (o.n.)
Yield: 71%
Spectra:
MS m/z: 428, 430(MI); 371, 373(MI-t-butyl); 297, 299(MI-TBDiMSiO)
¹H NMR (200 MHz, CDCl₃): δ0.13 (s, Si(CH₃)₂); 0.94 (s,t-butyl); 2.50 (s, SCH₃); 4.89 (s, CH₂O); 6.88–7.47 (thiophene and phenyl protons).

PREPARATION OF YLIDE KETONE

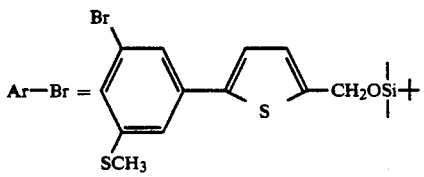

Conditions:
1) t-BuLi/THF; −78° to −20° (5 min)
2) MgBr₂/THF; −20°; 5 min
3) Pyridylthioester; 0°; 5 hours
Yield: 41%
Spectra:
MS m/z: 949(MI+2); 262(Ph₃P).
¹H NMR (400 MHz, CDCl₃): δ0.14 (s, Si(CH₃)₂); 0.94 (s,t-butyl); 1.16 (d, CH₃); 2.55 (s, SCH₃); 5.76–5.98 (m, CH₂=CH—CH₂—).

DESILYLATION TO CARBINOL YLIDE KETONE

Conditions:
1) aq. HCl/MeOH
2) 0°; 1 h
Yield: 86%
Spectra:
MS m/z: 555(MI-Ph₃PO); 262(Ph₃P).
¹H NMR (300 MHz, CDCl₃): δ1.15 (d, CH₃); 2.54 (s, SCH₃); 5.74–6.0 (m, CH₂=CH—CH₂—).

CYCLIZATION TO METHYLTHIOCARBAPENEM CARBINOL

Conditions: Benzene; 80°; o.n.
Yield: 83%
Spectra:
MS m/z: 555(MI); 385 (MI-β-lactam cleavage).
IR: 1787 (β-lactam C=O); 1750 and 1725 (other C=O's)
¹H NMR (300 MHz, CDCl₃): δ1.49 (d, CH₃); 1.80 (t, OH); 2.50 (s, SMe); 3.43 (dd, H6); 4.30 (m, H5); 5.76–6.0 (m, CH₂=CH—CH₂—); 6.97–7.40 (phenyl and thiophene protons).

OXIDATION TO SULFOXIDE AND SULFONE

Conditions:
1) excess m-ClPBA; aq. NaHCO₃/CH₂Cl₂
2) 0°; 1 hour
3) aq. Na₂S₂O₃; 0°; 2 hrs.
Yield:
52% Sulfoxide
32% Sulfone
Spectra (for sulfoxide):
¹H NMR (400 MHz, CDCl₃): δ1.48 (d, CH₃); 1.86 (t, OH); 2.76 (CH₃—S(O)—); 3.45 (dd, H6); 4.32 (m, H5); 4.84 (d, CH₂OH); 7.0–7.78 (thiophene and phenyl protons).

Spectra (for sulfone):
¹H NMR (400 MHz, CDCl₃): δ1.49 (d, CH₃); 1.85 (t, OH); 3.09 (s, CH₃—SO₂—); 3.47 (d, H6); 4.34 (m, H5); 4.85 (d, CH₂OH); 7.01–8.06 (thiophene and phenyl protons).

QUATERNIZATION OF CARBINOL

Conditions:*
1) 2.4–2.6 eq. 1-methylimidazole/CH₂Cl₂
2) 1.2–1.3 eq. triflic anhydride
3) 0°; 45 min
*identical for CH₃S(O)ₙ where n=0, 1, 2
Yield:
methylthio (97%)
methylsulfinyl (82%);
methylsulfonyl (84%).
Spectra:
¹H NMR (400 MHz, CDCl₃) of methylthio: δ1.48 (d, CH₃); 2.50 (s, SCH₃); 3.45 (dd, H6); 3.97 (CH₃N); 6.15–7.35 (thiophene, phenyl and two imidazole protons); 9.38 (N=CH—N).

Methylsulfinyl and methylsulfonyl quaternaries used immediately.

DEALLYLATION OF METHYLTHIO, METHYLSULFINYL, AND METHYLSULFONYL CARBAPENEMS

Conditions: 1) PPh₃; Pd(PPh₃)₄

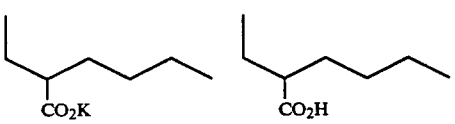

| | Solvent | T | Time | Yield |
|---|---|---|---|---|
| methylthio | 2:1 CH₂Cl₂:Et₂O | 0° | 2h | 16% |
| methylsulfinyl | 1:1 CH₂Cl₂:DMF | r.t. | 2h | 19% |
| methylsulfonyl | 1:1 CH₂Cl₂:DMF | r.t. | 2h | 26% |

Spectra:
¹H NMR (400 MHz, 2:1 D₂O:CD₃CN) of methylthio: δ1.53 (d, CH₃CHO—); 2.76 (s, SCH₃); 3.67 (dd, H6); 4.10 (N—CH₃); 5.81 (thiophene —CH₂—⁺N); 7.47–7.78 (thiophene, phenyl, and two imidazole protons).

¹H NMR (400 MHz, 2:1 D₂O: CD₃CN) of methylsulfinyl: δ1.58 (d, CH₃CHOH—); 3.16 (s, SCH₃); 3.75 (dd, H6); 4.16 (s, CH₃N); 5.89 (thiophene —CH₂—⁺N); 7.60–8.13 (thiophene, phenyl, and two imidazole protons); 9.10 (s, N=CH—N).

¹H NMR (400 MHz, 2:1 D₂O:CD₃CN) of methylsulfonyl: δ1.55 (d, CH₃CHOH—); 3.51 (s, CH₃SO₂); 3.73 (dd, H6); 4.14 (s, CH₃N); 5.87 (thiophene —CH₂—⁺N); 7.59–8.25 (thiophene, phenyl, and two imidazole protons); 9.08 (⁺N=CH—N).

EXAMPLE 9

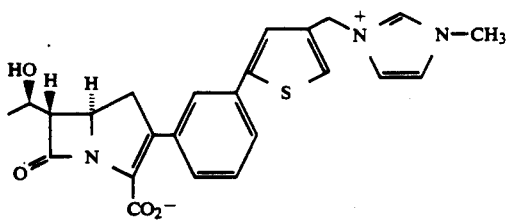

STARTING MATERIAL SYNTHESIS

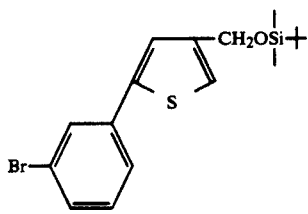

2-(3'-BROMOPHENYL)-4-(t-BUTLYDIMETHYL-SILYLOXYMETHYL) THIOPHENE

BROMINATION

Conditions: 3-thiophenecarboxylic acid (Aldrich) was selectively brominated to 5-bromo-3-thiophenecarboxylic acid using the method of Campaigne et al., J.A.C.S., 76, 2445 (1954).

Yield: 53%

$^1$H NMR (400 MHz, CDCl$_3$): δ7.51 (d, J=1.5 Hz); 8.11 (d, J=1.5 Hz).

REDUCTION TO 2-BROMO-4-THIOPHENEMETHANOL

Conditions:
1) excess BH$_3$∩Me$_2$S/THF
2) 0° to r.t.; o.n.
3) MeOH; 0°; slow addition then 15 min.

Yield: 82%

Spectra:
MS m/z MI (192, 194).

$^1$H NMR (400 MHz, CDCl$_3$): δ1.68 (t, OH); 4.61 (br. d, CH$_2$OH); 7.05 (br. d); 7.11(m), when decoupled at CH$_2$OH— 1.67 (s, OH); 7.04 and 7.11 (sh d's, J=1.5 Hz, thiophene protons).

CONDENSATION WITH 3-BROMOPHENYLBORONIC ACID

Conditions:
1) 2-bromo-4-thiophenemethanol/toluene
2) (Ph$_3$P)$_4$Pd
3) 3-bromophenylboronic acid/EtOH
4) aq. Na$_2$CO$_3$
5) 80°; 5-24 hours Yield: 43%

Spectra:
MS m/z: 268, 270 (MI); slight impurity (344, 346- dicondensation product)

$^1$H NMR (400 MHz, CDCl$_3$): δ1.67 (t, OH); 4.69 (d, CH$_2$OH); 7.20-7.74 (thiophene and phenyl protons).

SILYLATION

Conditions:
1) TBDMSiCl; Et$_3$N; DMF/CH$_2$Cl$_2$
2) 0° to r.t.; few hours

Yield: 82%

Spectra:
MS m/z: 382, 384(MI); 325, 327(MI-t-butyl); 251, 253 (MI-OSiMe$_2$t-butyl).

$^1$H NMR (400 MHz, CDCl$_3$): δ0.12 (s, Si(CH$_3$)$_2$); 0.96 (s, t-butyl); 4.72 (s, CH$_2$O—); 7.13-7.73 (thiophene and phenyl protons).

PREPARATION OF YLIDE KETONE

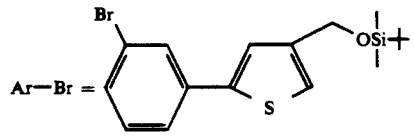

Conditions:
1) Mg; BrCH$_2$CH$_2$Br/THF; rflx; 2 hours
2) Pyridylthioester; 0°; 3 hours Yield: 45%

Spectra:
MS m/z: 908[MI+7(Li)]; 262 (Ph$_3$P).

$^1$H NMR (400 MHz, CDCl$_3$): δ0.13 (s, Si(CH$_3$)$_2$); 0.95 (s, t-butyl); 1.17 (d, CH$_3$); 5.78-6.06 (m, CH$_2$=CH—CH$_2$—).

DESILYLATION OF YLIDE KETONE CARBINOL

Conditions:
1) aq. HCl/MeOH
2) 0°; 1 hour

Yield: 94%

Spectra:
MS m/z: 794[MI+7(Li)]; 262 (Ph$_3$P).

$^1$H NMR (400 MHz, CDCl$_3$): δ1.16 (d, CH$_3$); 2.80 (dd, H6); 4.71 (d, CH$_2$OH); 5.77-5.89 (m, CH$_2$=C$\underline{H}$—CH$_2$—).

QUATERNIZATION OF CARBINOL

Conditions:
1) 2.5 eq. 1-methylimidazole/CH$_2$Cl$_2$
2) 1.26 eq triflic anhydride
3) 0°; 45 min Yield: 86% (crude); no data; used immediately.

DEALLYLATION

Conditions: PPh$_3$; Pd(PPh$_3$)$_4$

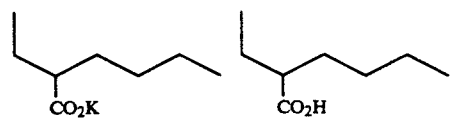

1:1:1 CH$_2$Cl$_2$:EtOAc:DMF; r.t.; 2 hours

Yield: 16%

Spectra:
UV(H$_2$O): λ max=290 mμ

$^1$H NMR (400 MHz, 2:1 D$_2$O:CD$_3$CN): (no internal standard —DOH at 4.80); δ1.52 (d, CH$_3$CHOH—); 3.64 (dd, H6); 4.08 (CH$_3$N); 5.58 (s, thiophene-CH$_2$);

7.55–7.91 (thiophene, phenyl, and two imidazole protons); 8.99 (s, N=CH—N).

EXAMPLE 10

STEP A1:

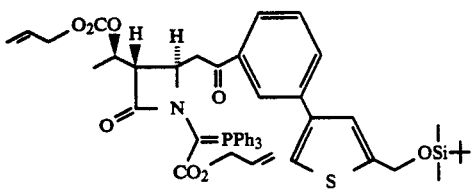

Yield: 53%
Spectra:
MS: m/z 901(MI); 262 (Ph₃P).
IR(CH₂CL₂): 1740 (carbonyls); 1620 (ylid) cm⁻¹
$^1$H NMR (300 MHz, CDCl₃): selected absorbances δ0.14 (s, Si(CH₃)₂); 0.94 (s, t-butyl Si); 1.16 (d, J=6 Hz, C$\underline{H}$₃CHOSi—); 2.79 (dd, H6); 4.90 (s, CH₂OSi—); 5.75–6.00 (m, two —CH₂CH=CH₂); 7.11–8.21 (all aromatic protons.)

STEP A2:

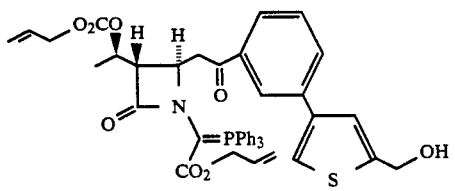

Yield: 80%
Spectra:
MS m/z 787 (MI); 509 (MI-Ph₃PO); 262 (Ph₃P).
IR 2965 (CH₂Cl₂): 3600 (OH); 1740 (carbonyls, 1740 cm⁻¹
$^1$H NMR (300 MHz, CDCl₃): δ selected absorbances 1.15 (d, J=6 Hz, C$\underline{H}$₃CHO—); 2.78 (dd, J=2 and 10 Hz, H6); 4.87 (s, C$\underline{H}$₂OH); 5.74–6.00 (m two —CH₂—C$\underline{H}$=CH₂).

STEP B:
Yield: 49%
Spectra:
IR(CH₂Cl₂): 1780 (β-lactam); 1740 and 1715 (carbonate and ester (cm⁻¹).
$^1$H NMR (300 MHz, CDCl₃): δ1.49 (d, J=6 Hz, C$\underline{H}$₃CHO—); 1.85 (t, J=6 Hz, OH); 3.13(dd, J=10 and 18 Hz, H$_{1a}$); 3.32 (dd, J=9 and 18 Hz, H$_{1b}$); 3.43 (dd, J=3 and 8 Hz, H6); 4.59–4.74 (m's, two CH₂CH=CH₂); 4.88 (d, J=6 Hz, C$\underline{H}$₂OH); 5.13–5.40 (m, two CH₂CH=CH₂); 5.76–6.01 (m, two CH₂C$\underline{H}$=CH₂); 7.24–7.55 (m's, phenyl and thienyl protons).

STEP C:

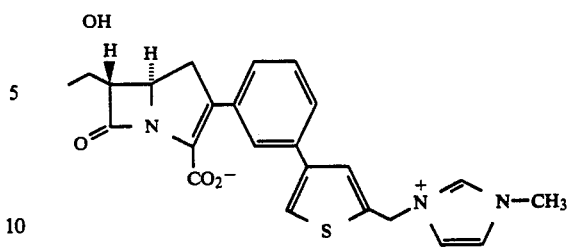

Yield: 21%
Spectra:
UV(H₂O): $\lambda_{max}$=265 mμ; $\lambda_{sh}$=303 mμ (NH₂OH quenchable); ε=8,800.
$^1$H NMR (300 MHz, D₂O): δ1.26 (d, J=6 Hz, CH₃CHO—); 2.98 (dd, J=10 and 18 Hz, H$_{1a}$); 3.34 (dd, J=8 and 18 Hz H$_{1b}$); 3.42 (dd, J=2.5 and 6 Hz, H6); 3.79 (s, NCH₃); 4.20 (m's, H5 and H$_{1'}$); 5.52 (s, thiophene-CH₂—N); 7.11–7.60 (phenyl, thiophene and two imidazole protons); 8.72 (s, N=C$\underline{H}$—N of imidazole).

PREPARATION OF INTERMEDIATES

STEP A:

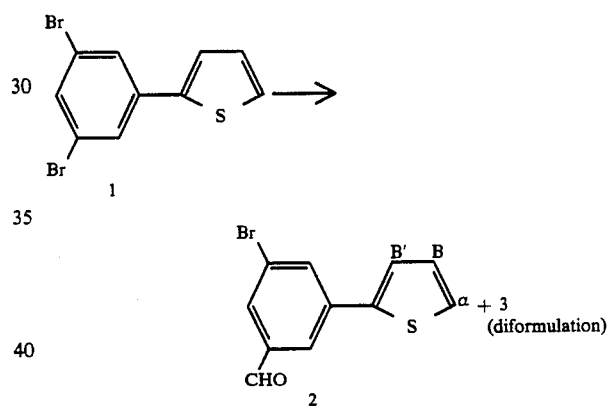

To a solution of 1 (2.86 g, 9 mmol) in THF (30 ml) with stirring at −78° under N₂, 1.6M BuLi (5.8 ml, 9.3 mmol) was added dropwise via an addition funnel. After a few mins for the addition and 5 min additional stirring, DMF (0.9 ml, 116 mmol) was added, and the reaction was allowed to warm to ambient temperature. Stirring was continued for 3 h. The yellow solution was then poured into brine (200 ml) and Et₂O (100 ml), shaken, and separated. The aqueous layer was again extracted with Et₂O, and the combined organic layers were washed with 1:1 brine/H₂O (100 ml), dried (MgSO₄), filtered and concentrated in vacuo to a yellow liquid with a tan precipitate. Hexane (a few ml) was added, and the residue was slurried and filtered. The insoluble portion was washed 2× with hexane (few ml), and the solid dried in vacuo to give 3 (496 mg, 19% yield). The hexane-soluble filtrate was re-concentrated in vacuo (2.38 g) and chromatographed on 60 g of Bakers Si gel (60–200M Hz) packed in hexane. The material was applied to the column in 1:2 CH₂Cl₂/hexane and eluted with the same solvent system (300 ml) after which 10% Et₂O in hexane was used to elute 2. Approximately 814 mg of 2 was eluted, but 630 mg of that required further purification on 1000μ Si Gel GF plates (eluting and extracted with CH$_2$Cl$_2$) to provide a total of purified 2 (713 mg, 30% yield)

Data for 2:

MS: m/z 266/268 (MI)

$^1$H NMR (300M Hz, CDCl$_3$): δ7.06 (dd, J=4 and 6, H$_\beta$); 7.32 (dd, J=0.5 and 6 Hz, H$_\alpha$); 7.33 (dd, J=0.5 and 4 Hz, B$_{\beta'}$); 7.82, 7.90 and 7.96 (3 m's, 3 phenyl H's); 9.93 (s, CHO)

Data for 3:

MS: m/z 294/296 (MI)

$^1$H NMR (300 MHz, CDCl$_3$): δ7.43 and 7.73 (2 d's, J=4 Hz, H$_\beta$ and H$_{\beta'}$): 7.95, 7.97 and 8.01 (3 m's, 3 phenyl H's); 9.87 and 9.94 (2s's, 2 CHO's).

STEP B:

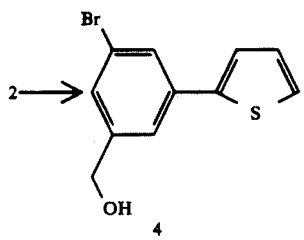

To a solution of 2 (707 mg, 2.7 mmol) in MeOH(26 ml) with stirring at 0° was added NaBH$_4$ (125 mg, 3.3 mmol), and after some initial foaming, stirring was continued at 0° for 35 min. The reaction mixture was concentrated to a small volume of yellow oil under a N$_2$ stream. Et$_2$O (30 ml) and brine (30 ml) were added, and the reaction mixture was shaken in a separatory funnel. After phase separation, the aqueous layer was again extracted with ether. The combined organic layers were backwashed with brine, dried (MgSO$_4$), filtered and concentrated in vacuo to give the crude alcohol (735 mg) as an off-white solid. Preparative TLC of 304 mg of this substance on 4–1000μ Si Gel GF plates (eluting with 5% EA/CH$_2$Cl$_2$ and extracting with 10% MeOH/CH$_2$Cl$_2$) provided purified alcohol 4 (278 mg).

$^1$H NMR (30M Hz, CDCl$_3$): δ472 (s, CH$_2$OH); 7.06 (m, 4'''—H of thiophene); 7.30 (m, 3''' and 5'''—H's of thiophene); 7.42, 7.50 and 7.66 (3 br m's, phenyl H's).

EXAMPLE 19

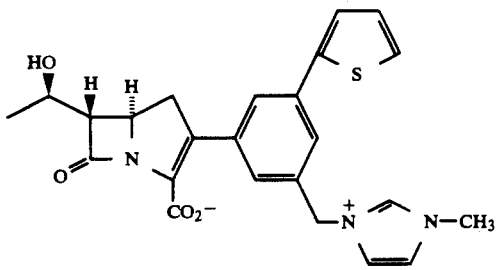

SILYLATION OF
2-(3'-BROMO-5'-HYDROXYMETHYL)PHENYL-THIOPHENE

Conditions:
1) TBDMSiCl; Et$_3$N; DMF/CH$_2$Cl$_2$
2) overnight
Yield: 80%
Spectra:

MS m/z 382, 384 (MI); 325, 327 (MI-t-butyl); 251, 253 (MI-(CH$_3$)$_2$t-BuSiO—).

$^1$H NMR (300 MHz, CDCl$_3$): δ0.12 (s, t-butyl); 0.96 (s, Si(CH$_3$)$_2$); 4.73 (s, CH$_2$O); 7.06–7.62 (thiophene and phenyl protons).

PREPARATION OF YLIDE KETONE

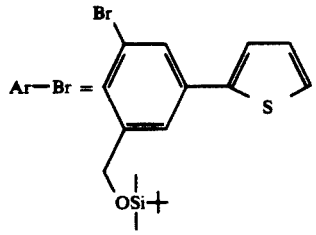

Conditions:
1) Mg; BrCH$_2$CH$_2$Br/THF; rflx; 2 hours
2) Pyridylthioester; 0°; 2 hours
Yield: 33%
Spectra:

$^1$H NMR (300 MHz, CDCl$_3$): δ(mixture of correct product and diaddition of Grignard) 0.12 and 0.14 (2s, t-butyls); 0.96 and 0.97 (2s; Si(CH$_3$)$_2$); 1.15 (d, CH$_3$).

DESILYLATION TO CARBINOL YLIDE KETONE

Conditions:
1) aq. HCl/MeOH
2) 0°; 1 hour
3) prep. TLC in 1:1 EtOAC:CH$_2$Cl$_2$ to remove diaddition product
Yield: 74% of carbinol
Spectra:

MS m/z: 787 (MI); 509 (MI-Ph$_3$PO); 262 (Ph$_3$P)

$^1$H NMR (300 MHz, CDCl$_3$): δ1.16 (d, CH$_3$); 5.75–6.01 (m, CH$_2$=CH—CH$_2$—)

CYCLIZATION OF YLIDE CARBINOL TO CARBAPENEM CARBINOL

Conditions: Benzene; 80°; overnight
Yield: 83%
Spectra:

MS m/z: 509 (MI); 339 (β-lactam cleavage).

IR: 1780 (β-lactam C=O); 1745 and 1720 (C=O's) cm$^{-1}$ $^1$H NMR (300 MHz, CDCl$_3$): δ1.49 (d, CH$_3$); 1.84 (t, OH); 3.42 (dd, H); 4.30 (m, H$_5$); 5.75–6.00 (m, CH$_2$=CH—CH$_2$—); 7.06–7.56 (thiophene and phenyl protons).

QUATERNIZATION OF CARBINOL

Conditions:
1) 2.5 eq. 1-methylimidazole/CH$_2$Cl$_2$
2) 1.1 eq. triflic anhydride
3) 0°; 30 min
Yield:
94%
no data; used immediately

DEALLYLATION

Conditions: PPh$_3$; Pd(PPh$_3$)$_4$

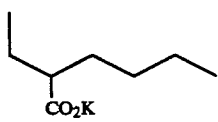

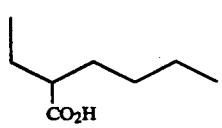

1:1 CH$_2$Cl$_2$: EtOAc; 2 hours
Yield: 20%
Spectra:
UV(H$_2$O): λmax=293 mμ
$^1$H NMR (300 MHz, 2:1 D$_2$O:CD$_3$CN): (no internal standard—DOH at 4.80); δ1.55 (d, C$\underline{H}_3$CHOH—); 4.12 (s, N—CH$_3$); 5.63 (s, thiophene—C$\underline{H}_2$); 4.03 (s, N=CH—N).

EXAMPLE 30
STEP A

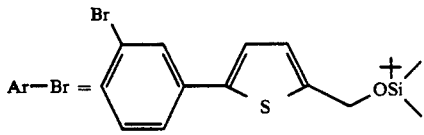

Conditions:
A1:
1) Mg/THF; 3 hrs./R.T.
2) 0°; 15 min; THF; pyridylthioester
Yield: 67%
Conditions:
A2: CH$_3$OH/H$_2$SO$_4$; 0°; 1.25 hrs
Yield: 81%
STEP B
Conditions
B1: Xylene; 130°; 1.5 hrs.
Yield: 83%
Conditions
B2: Triflic anhydride; CH$_2$Cl$_2$;

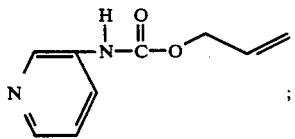

B2: 0°; 15 min.
Spectra:
IR: 1775; 1740
NMR: H6: 3.43-3.52; dd; J=3 and 8 Hz H5: 4.24-4.38; ddd; J=3, 9 and 10 Hz CH$_2$N$^+$: 5.78 (s); Aromatic H's: 7.2-9.65
STEP C
Conditions: PPh$_3$; Pd(PPh$_3$)$_4$;

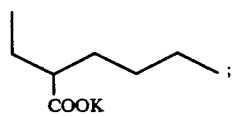

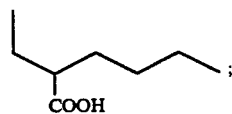

CH$_2$Cl$_2$; 0°; 4 hrs
Yield: 19%
UV: 298
ε ext 2397

EXAMPLE 31
STEP A

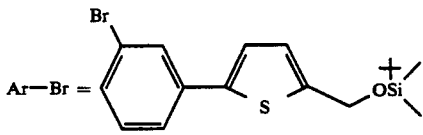

Conditions A:
1) Mg/THF 3 hr./R.T.
2) 0°; 15 min THF pyridylthioester
Yield of A: 67%
Conditions A2: CH$_3$OH/H$_2$SO$_4$ 0°; 1.25 hr
Yield of A2: 81%
STEP B
Conditions:
B1; Xylene; 130°; 1.5 hrs.
Yield: 83%
Conditions:
B2: Triflic anhydride; CH$_2$Cl$_2$;

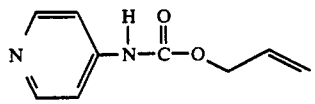

0°; 15 min.
STEP C
Conditions: PPh$_3$; Pd(PPh$_3$)$_4$:

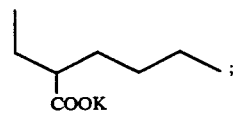

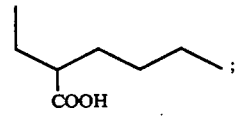

CH$_2$Cl$_2$; 0°; 4 hrs.
UV: 287
ε ext 1107

EXAMPLE 32

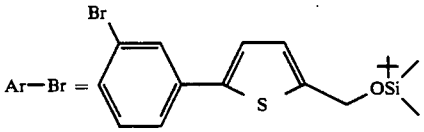

STEP A
Conditions:
A1:
1) Mg/THF; 3 hr.s/R.T.
2) 0°; 15 min; THF; pyridylthioester
Yield: 67%
Conditions:
A2: CH₃OH/H₂SO₄; 0°; 1.25 hrs.
Yield: 81%
STEP B
Conditions:
B1: Xylene; 130°; 1.5 hrs.
Yield: 83%
Conditions:
B2: Triflic anhydride; CH₂Cl₂;

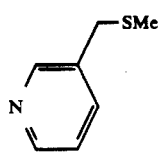

0°; 15 min.
Spectra:
IR: 1780; 1745; 1715
NMR: SCH₃: 2.02(s); H6: 3.42–3.52; dd; J=3 and 8 Hz H5: 4.24–4.40; ddd; J=3, 9 and 9 Hz SCH₂: 3.88 (s); NCH₂: 6.12(s); Aromatic H's: 7.22–9.02

STEP C
Conditions: PPh₃; Pd(PPh₃)₄;

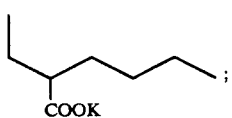

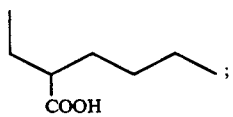

CH₂Cl₂
Yield: 14%
UV: 293
ε ext: 3847

What is claimed is:
1. A compound of the formula:

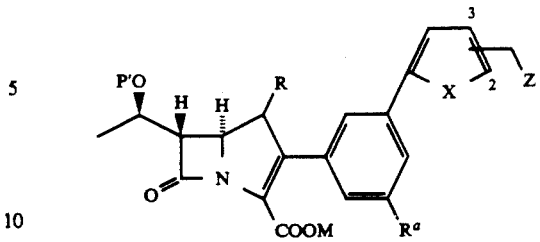

wherein;
R is H or CH₃;
P' is a removable protecting group for hydroxy;
M is a removable protecting group for carboxy;
Rᵃ is selected from the group consisting of H, OP', Cl, Br, I, SCH₃, CN, CHO, SOCH₃, SO₂CH₃, CO₂M, CH₂OP' or CONH₂; and with the proviso that the —CH₂Z substituent is in the 2- or 3-position of the heteroaromatic ring;
X is O or S, and
Z is a leaving group selected from the group consisting of alkylsulfonyloxy, substituted alkylsulfonyloxy, arylsulfonyloxy, substituted arylsulfonyloxy, fluorosulfonyloxy, and halogen.

2. The compound of claim 1 where M is selected from the group consisting of alkyl, substituted alkyl, benzyl, substituted benzyl, aryl, substituted aryl, allyl, substituted allyl, and triorganosilyl.

3. The compound of claim 1 wherein M is selected from the group consisting of benzhydryl, p-nitrobenzyl, 2-naphthylmethyl, allyl, 2-chloroallyl, benzyl, 2,2,2-trichloroethyl, trimethylsilyl, t-butyldimethylsilyl, t-butyldiphenylsilyl, 2-(trimethylsilyl)ethyl, phenacyl, p-methoxybenzyl, acetonyl, o-nitrobenzyl p-methoxyphenyl, 4-pyridylmethyl and t-butyl.

4. The compound of claim 1 wherein P' is selected from the group consisting of trialkylsilyl, aryl(alkyl)alkoxysilyl, alkoxy(diaryl)silyl, diarylalkylsilyl, alkyloxycarbonyl, substituted alkyloxycarbonyl, benzyloxycarbonyl, substituted benzyloxycarbonyl, allyloxycarbonyl and substituted allyloxycarbonyl.

5. The compound of claim 1 wherein P' is selected from the group consisting of t-butylmethoxyphenylsilyl, t-butoxydiphenylsilyl, trimethylsilyl, triethylsilyl, t-butyldimethylsilyl, o-nitrobenzyloxycarbonyl, p-nitrobenzyloxycarbonyl, benzyloxycarbonyl, t-butyloxycarbonyl, 2,2,2-trichloroethyloxycarbonyl and allyloxycarbonyl.

6. The compound of claim 1 wherein Z is selected from the group consisting of methanesulfonyloxy, trifluoromethanesulfonyloxy, fluorosulfonyloxy, p-toluenesulfonyloxy, 2,4,6-triisopropylbenzenesulfonyloxy, p-bromobenzenesulfonyloxy, p-nitrobenzenesulfonyloxy, chloro, bromo, and iodo.

* * * * *